(12) United States Patent
Stober et al.

(10) Patent No.: US 11,735,291 B2
(45) Date of Patent: Aug. 22, 2023

(54) QUANTUM COMPUTING THERMODYNAMIC OBSERVABLES OF A CHEMICAL SYSTEM

(71) Applicants: International Business Machines Corporation, Armonk, NY (US); EXXON MOBIL RESEARCH AND ENGINEERING COMPANY, Annandale, NJ (US)

(72) Inventors: Spencer Troy Stober, Bethlehem, PA (US); Stuart Maxwell Harwood, Jersey City, NJ (US); Don Greenberg, New York City, NY (US); Tanvi Pradeep Gujarati, San Jose, CA (US); Sarah Mostame, Scarsdale, NY (US); Sumathy Raman, Annandale, NJ (US); Dimitar Vasilev Trenev, Sleepy Hollow, NY (US)

(73) Assignees: INTERNATIONAL BUSINESS MACHINES CORPORATION, Armonk, NY (US); EXXON MOBIL RESEARCH AND ENGINEERING COMPANY, Annandale, NJ (US)

( * ) Notice: Subject to any disclaimer, the term of this patent is extended or adjusted under 35 U.S.C. 154(b) by 571 days.

(21) Appl. No.: 16/723,086

(22) Filed: Dec. 20, 2019

(65) Prior Publication Data
US 2021/0193270 A1    Jun. 24, 2021

(51) Int. Cl.
*G01N 33/48* (2006.01)
*G01N 33/50* (2006.01)
(Continued)

(52) U.S. Cl.
CPC .............. *G16C 10/00* (2019.02); *G06F 17/11* (2013.01); *G06N 10/00* (2019.01); *G16C 20/10* (2019.02); *G16C 20/20* (2019.02)

(58) Field of Classification Search
CPC ........ G16C 10/00; G16C 20/10; G16C 20/20; G16C 20/30; G16C 20/90; G06F 17/11; G06N 10/00; G06N 5/003
See application file for complete search history.

(56) References Cited

U.S. PATENT DOCUMENTS

| 8,140,467 B2 | 3/2012 | Kasai et al. |
| 8,301,390 B2 | 10/2012 | Sastry et al. |
(Continued)

OTHER PUBLICATIONS

Strekalov ML. On the partition function of Morse oscillators. Chemical Physics Letters, vol. 393, pp. 192-196. (Year: 2004).*
(Continued)

*Primary Examiner* — Russell S Negin
(74) *Attorney, Agent, or Firm* — Amin, Turocy & Watson, LLP

(57) ABSTRACT

Techniques regarding determining thermodynamic observables of a chemical system are provided. For example, one or more embodiments described herein can include a system, which can comprise a memory that can store computer executable components. The system can also include a processor, operably coupled to the memory, and that can execute the computer executable components stored in the memory. The computer executable components can include a potential energy component that can fit a potential energy function to a computed potential energy surface of a molecule. The computer executable components can also include a vibrational mode component that can compute an intramolecular vibrational mode of the molecule based on the potential energy surface fitted with the potential energy function. Also, the computer executable components can include a partition component that can compute a partition function based on the intramolecular vibrational mode.

25 Claims, 18 Drawing Sheets
(4 of 18 Drawing Sheet(s) Filed in Color)

(51) Int. Cl.
G16C 10/00 (2019.01)
G16C 20/20 (2019.01)
G06F 17/11 (2006.01)
G06N 10/00 (2022.01)
G16C 20/10 (2019.01)

(56) References Cited

U.S. PATENT DOCUMENTS

| | | |
|---|---|---|
| 2007/0198199 A1 | 8/2007 | Mills |
| 2007/0239366 A1 | 10/2007 | Hilton et al. |
| 2009/0182542 A9 | 7/2009 | Hilton et al. |
| 2015/0142398 A1 | 5/2015 | Miller et al. |
| 2018/0096085 A1 | 4/2018 | Rubin |
| 2018/0275758 A1 | 9/2018 | Reiher et al. |

OTHER PUBLICATIONS

Davies PCW. Does quantum mechanics playa non-trivial role in life? BioSystems, vol. 78, pp. 69-79. (Year: 2004).*
Viswanathan KS. Amharmonicity of vibration in molecules. Proceedings of the Indian Academy of Sciences, pp. 85-97. (Year: 1958).*
Giese et al. Extension of adaptive tree code and fast multipole methods to high angular momentum particle charge densities. Journal of Computational Chemistry, vol. 29, 20 pages. (Year: 2009).*
Keshavarzzadeh et al. Numerical integration in multiple dimensions with designed quadrature. arXiv:1804.06501v1, 29 pages, Apr. 17, 2018.*
McCaskey et al. Quantum chemistry as a benchmark for near-term quantum computers. Nature Quantum Information. vol. 5, Nov. 15, 2019, 8 pages.*
Cao, et al. "Quantum Chemistry in the Age of Quantum Computing." arXiv:1812.09976v2 [quant-ph] Dec. 28, 2018, 194 pages.
Piasecki, et al. "Prediction of equilibrium distributions of isotopologues for methane, ethane and propane using density functional theory." Geochimica et Cosmochimica Acta, 190, 1-12. doi:10.1016/j.gca.2016.06.003, 2016. 12 pages.
Crooks. "Gradients of parameterized quantum gates using the parameter-shift rule and gate decomposition. arXiv preprint." arXiv:1905.13311v1 [quant-ph] May 30, 2019. 5 pages.
Bertsekas, et al. "Gradient Convergence in Gradient Methods With Errors." SIAM Journal on Optimization, 10(3):627-642, 2000. 16 pages.
Kandala, et al. "Hardware-efficient Variational Quantum Eigensolver for Small Molecules and Quantum Magnets." Nature, 549:242, 2017. arXiv:1704.05018v2 [quant-ph] Oct. 13, 2017. 24 pages.
Peruzzo, et al. "A variational eigenvalue solver on a photonic quantum processor." Nature Communications, 5(1):4213, 2014. arXiv:1304.3061v1 [quant-ph] Apr. 10, 2013. 10 pages.
Shen, et al. "Quantum Implementation of Unitary Coupled Cluster for Simulating Molecular Electronic Structure." Physical Review A, 95(2):020501, 2017. 6 pages.
Hempel, et al. "Quantum Chemistry Calculations on a Trapped-Ion Quantum Simulator." Physical Review X, 8(3):031022, 2018. 22 pages.
Colless, et al. "Computation of Molecular Spectra on a Quantum Processor with an Error-Resilient Algorithm." Physical Review X, 8(1):011021, 2018. 7 pages.
Santagati, et al. "Witnessing eigenstates for quantum simulation of hamiltonian spectra." 4(1):9646, 2018. 12 pages.
Aspuru-Guzik, et al. "Simulated Quantum Computation of Molecular Energies." 309(5741):1704, 2005. doi: 10.1126/science.1113479. URL http://science.sciencemag.org/content/309/5741/1704.abstract. 21 pages.
Barkoutsos, et al. "Quantum algorithms for electronic structure calculations: Particle-hole hamiltonian and optimized wavefunction expansions." Phys. Rev. A 98, 022322—Published Aug. 20, 2018.
Bravyi, et al. "Tapering off qubits to simulate fermionic hamiltonians." arXiv:1701.08213v1 [quant-ph] Jan. 27, 2017. 15 pages.
O'Malley, et al. "Scalable Quantum Simulation of Molecular Energies." Physical Review X 6, 031007 (2016). 13 pages.
Hutchings, et al. "Tunable Superconducting Qubits with Flux-Independent Coherence." arXiv:1702.02253v2 [cond-mat.supr-con] Feb. 21, 2017. 17 pages.
Gearhart. "The rotational specific heat of molecular hydrogen in the old quantum theory." APS April Meeting, 2005. URL http://meetings.aps.org/link/BAPS.2005.APR.K11.1. 83 pages.
Dennison. "A Note on the Specific Heat of the Hydrogen Molecule." Proceedings of the Royal Society of London. Series A, Containing Papers of a Mathematical and Physical Character, 115(771):483{486, 1927. doi: 10.1098/rspa.1927.0105. URL https://doi.org/10.1098/rspa.1927.0105. 4 pages.
Chase. "NIST-JANAF Themochemical Tables." Fourth Edition. J. Phys. Chem. Ref. Data, Monograph 9, 1998. 1961 pages.
Moll, et al. "Quantum optimization using variational algorithms on near-term quantum devices." Quantum Sci. Technol. 3 (2018) 030503. 18 pages.
Bravyi, et al. "Fermionic Quantum Computation." Annals of Physics 298, 210-226 (2002). 17 pages.
Seeley, et al. "The Bravyi-Kitaev transformation for quantum computation of electronic structure." The Journal of Chemical Physics 137, 224109 (2012); doi: 10.1063/1.4768229. 17 pages.
Seita, et al. "Reducing qubit requirements for quantum simulation using molecular point group symmetries." arXiv:1910.14644v1 [quant-ph] Oct. 31, 2019. 6 pages.
Wannier. "Statistical Physics." Dover Publ., 1987. Orig. publ. by Wiley, 1966. 564 pages.
Cornish, et al. "The Specific Heat of Hydrogen Gas At Low Temperatures From the Velocity of Sound; and a Precision Method of Measuring the Frequency of an Oscillating Circuit." Journal of the American Chemical Society, vol. 50, Issue 3, 1928. 26 pages.
McQuarrie. "Statistical Mechanics." Harper Row, 1976. 657 pages.
Mell, Peter, et al. "The NIST Definition of Cloud Computing." National Institute of Standards and Technology. Sep. 2011. 7 pages.
Bonhoeffer, et al. "About para and orthohydrogen, Uber Para- und Orthowasserstoff." ChemistryPublished 2016 DOI:10.1515/zpch-1929-0408; https://www.semanticscholar.org/paper/%C3%9Cber-Para-und-Orthowasserstoff-Bonhoeffer-Harteck/
171b155a8e2cc66775b149af96296d0b5f3729d9, Last Accessed Dec. 12, 2019. Zeitschrift fur Physikalische Chemie,B(1):113, 1929. 31 pages.
Jordan, et al. "About the Paulische equivalence ban, Über das Paulische Äquivalenzverbot." PhysicsPublished 1993 DOI:10.1007/978-3-662-02781-3_9, https://link.springer.com/chapter/10.1007%2F978-3-662-02781-3_9, Last Accessed Dec. 12, 2019, Z. Phys, 47(9-10):631, 1928. doi:10.1007/BF01331938. 14 pages.

* cited by examiner

QUANTUM COMPUTING THERMODYNAMIC OBSERVABLES OF A CHEMICAL SYSTEM

BACKGROUND

The subject disclosure relates to quantum-based computing of one or more thermodynamic observables of a chemical system, and more specifically, to computing one or more thermodynamic observables on noisy intermediate-scale quantum devices with chemical accuracy.

Accurate thermodynamic properties of chemical systems underpin process engineering. When thermodynamic observables cannot be measured experimentally, computational chemistry and statistical mechanics can be utilized, which traditionally include: (i) calculation of the Born-Oppenheimer potential energy surface ("BOPES"); (ii) determination of intramolecular vibrational modes; and (iii) calculation of the partition function and thermodynamic observables as a function of temperature and/or pressure. Traditionally, the first step can result in a computational bottleneck at least because it involves solving the Schrodinger equation for a fixed position of nuclear coordinates, a task that quantum computers have the potential to accelerate beyond what is possible using classical computers.

By harnessing the quantum nature of matter, quantum computers have been constructed that can manipulate entanglement and superposition of qubits to represent, and operate on, different quantum states. In conjunction with hybrid quantum-classical algorithms, and various simplifying assumptions, these machines can efficiently approximate solutions to the Schrodinger equation. Traditionally, noisy intermediate-scale quantum devices have been used to compute the BOPES of small molecular systems, such as HeH+, $H_2$, LiH, and/or $BeH_2$. However, these calculations are often too noisy for the determination of rotational and vibrational wavenumbers using traditional methods, such as constructing the Hessian by finite differences and finding its eigenvalues and eigenvectors. Therefore, these calculations would not be suitable for use in obtaining thermodynamic observables of the studied molecules.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, computer-implemented methods, apparatuses and/or computer program products that can regard quantum-based computing of one or more thermodynamic properties of a chemical system are described.

According to an embodiment, a system is provided. The system can comprise a memory that can store computer executable components. The system can also comprise a processor, operably coupled to the memory, and that can execute the computer executable components stored in the memory. The computer executable components can comprise a potential energy component that can fit a potential energy function to a computed potential energy surface of a molecule. The computer executable components can also comprise a vibrational mode component that can compute an intramolecular vibrational mode of the molecule based on the potential energy surface fitted with the potential energy function. Also, the computer executable components can comprise a partition component that can compute a partition function based on the intramolecular vibrational mode. An advantage of such a system can be enabled use of quantum-based computing to derive the partition function and thermodynamic observables.

In some examples, the system can further comprise a variational quantum eigensolver component that can execute a variational quantum eigensolver algorithm on a quantum computer to compute the potential energy surface based on a Born-Oppenheimer approximation. The system can further comprise an optimizer component that can execute an optimization algorithm used in execution of the variational quantum eigensolver algorithm. An advantage of such a system can be the sharing of computational work amongst classical and quantum computing technologies to maximize efficiencies and minimize cost.

According to another embodiment, a system is provided. The system can comprise a memory that can store computer executable components. The system can also comprise a processor, operably coupled to the memory, and that can execute the computer executable components stored in the memory. The computer executable components can comprise a computations component that can compute a partition function based on a Born-Oppenheimer potential energy surface computed via a variational quantum eigensolver algorithm. The computations component can also utilize a parameterized molecular potential energy function to mitigate noise inherent to a quantum device that executed the variational quantum eigensolver algorithm. An advantage of such a system can be a reduction in noise introduced to the resulting dissociation curve.

In some examples, the system can also comprise an observables component that can compute a thermodynamic observable based on the partition function. An advantage of such a system can be the determination of a chemical system's thermodynamic observables by leveraging the computing capabilities of quantum algorithms.

According to an embodiment, a computer-implemented method is provided. The computer-implemented method can comprise fitting, by a system operably coupled to a processor, a potential energy function to a computed potential energy surface of a molecule. The computer-implemented method can also comprise computing, by the system, an intramolecular vibrational mode of the molecule based on the potential energy surface fitted with the potential energy function. Further, the computer-implemented method can comprise computing, by the system, a partition function based on the intramolecular vibrational mode. An advantage of such a computer-implemented method can be that the fitted potential energy function can provide analytical solutions for vibrational energy levels of a molecule to facilitate computation of the partition function.

In some examples, the computer-implemented method can also comprise executing, by the system a variational eigensolver algorithm on a quantum computer to compute the potential energy surface based on a Born-Oppenheimer approximation. The computer-implemented method can also comprise executing, by the system, an optimization algorithm used in the execution of the variational quantum eigensolver algorithm. The optimization algorithm can implement at least one computation process selected from the group consisting of adaptive termination, resampling, customizable step length scheduling, and bootstrapping. An advantage of such a computer-implemented method can be improved computational times due at least to the one or more computation processes implemented by the optimization algorithm.

According to another embodiment, a computer-implemented method is provided. The computer-implemented method can comprise computing, by a system operably coupled to a processor, a partition function based on a Born-Oppenheimer potential energy surface computed via a variational quantum eigensolver algorithm. The computer-implemented method can also comprise utilizing, by the system, a parameterized molecular potential energy function to mitigate noise inherent to a quantum device that executed the variational quantum eigensolver algorithm. An advantage of such a computer-implemented method can be to ameliorate of noise inherent in single-point energy calculations on a noisy intermediate-scale quantum device.

In some examples, the computer-implemented method can also comprise fitting, by the system, a molecular potential energy function to the Born-Oppenheimer potential energy surface to derive the parameterized molecular potential energy function. The computer-implemented method can further comprise computing, by the system, an intramolecular vibrational mode based on the parameterized molecular potential energy function. Additionally, the computer-implemented method can comprise computing, by the system, the partition function based on the intramolecular vibrational mode. An advantage of such a computer-implemented method can be that the parameterized potential energy function can account for uneven spacing on vibrational energy levels and/or anharmonicity.

According to an embodiment, a computer program product for utilizing quantum computing to determine thermodynamic observables is provided. The computer program product can comprise a computer readable storage medium having program instructions embodied therewith. The program instructions can be executable by a processor to cause the processor to fit, by the processor, a potential energy function to a computed potential energy surface of a molecule. The program instructions can also cause the processor to compute, by the processor, an intramolecular vibrational mode of the molecule based on the potential energy surface fitted with the potential energy function. Further, the program instructions can cause the processor to compute, by the processor, a partition function based on the intramolecular vibrational mode. An advantage of such a computer program product can be the use of quantum computing to overcome computational constraints inherent in electronic structure determinations.

In some examples, the program instructions can further cause the processor to compute, by the processor, a thermodynamic observable of the molecule based on the partition function. The thermodynamic observable can be at least one member selected from the group consisting of entropy, internal energy, enthalpy, Gibbs free energy, heat capacity, constant volume heat capacity, constant pressure heat capacity, Helmholtz free energy, reaction rate, and a reaction equilibrium constant. An advantage of such a computer program product can be the utilization of variational quantum eigensolver algorithms to determine the thermodynamic observables of large and/or complex chemical systems.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
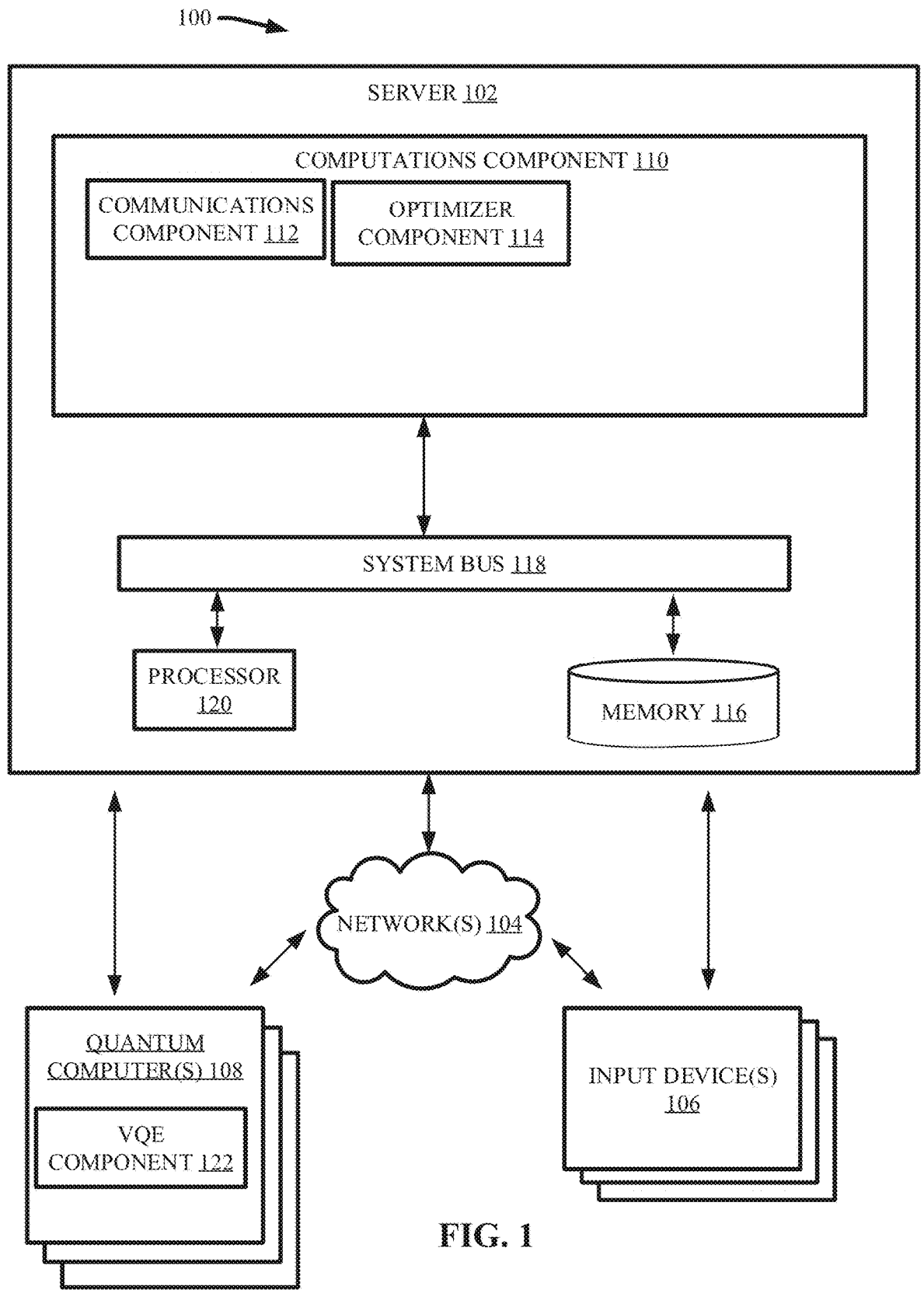
FIG. 1 illustrates a block diagram of an example, non-limiting system that can compute one or more thermodynamic observables of a chemical system using one or more variational quantum eigensolver ("VQE") algorithms in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Given the problems with other implementations of quantum-based computing of thermodynamic observables of a chemical system; the present disclosure can be implemented to produce a solution to one or more of these problems by incorporating various features that can mitigate the amount of noise added to the computations through: improvements to classical computer optimizers used in a variational quantum eigensolver algorithm, a qubit measurement error mitigation algorithm, and/or a parameterized molecular potential energy function to ameliorate the noise inherent in single-point energy calculations on quantum devices. Advantageously, one or more embodiments described herein can improve the chemical accuracy of the thermodynamic computations, as compared to conventional technologies. Further, the improved chemical accuracy can facilitate scaled implementation of the various embodiments to larger and/or more complex chemical systems than chemical systems analyzed by conventional quantum-based computing techniques.

Various embodiments of the present invention can be directed to computer processing systems, computer-implemented methods, apparatus and/or computer program products that facilitate the efficient, effective, and autonomous (e.g., without direct human guidance) quantum-based computing of one or more thermodynamic observables of a chemical system. For example, one or more embodiments described herein can comprise executing one or more VQE algorithms in combination with one or more analytical quantum gradient ("AQGD") optimizers, which can mitigate the introduction of noise (e.g., emerging from one or more hardware properties of the quantum computer executing the VQE algorithm) into the thermodynamic computations. Further, one or more embodiments can comprise parameterizing one or more molecular potential energy functions based on one or more VQE algorithms to compute one or more partition functions. Additionally, various embodiments can comprise computing various thermodynamic observables of the given chemical system based on the one or more partition functions.

For example, one or more embodiments can comprise executing a VQE algorithm on one or more superconducting qubit quantum computers to calculate the BOPES of a given chemical system. The BOPES can be utilized by one or more classical computer optimizers. Execution of the VQE algorithm can be facilitated by one or more optimization algorithms, such as AQGD optimizer, that can enable efficient and robust calculations of the dissociation curve. Further, various embodiments can compute one or more partition functions (e.g., such as vibrational partition functions) of the chemical system based on the one or more parameterized molecular potential energy functions, from which one or more thermodynamic observables (e.g., internal energy, entropy, heat capacity, and/or equilibrium constant) of the chemical system can be determined.

The computer processing systems, computer-implemented methods, apparatus and/or computer program products employ hardware and/or software to solve problems that are highly technical in nature (e.g., quantum-based computing of thermodynamic observables), that are not abstract and cannot be performed as a set of mental acts by a human. For example, an individual, or a plurality of individuals, cannot readily complete the vast amount of computations need to solve the Schrodinger equation for a fixed position of nuclear coordinates, as described in various embodiments herein. Further, one or more embodiments described herein can constitute a technical improvement over conventional computation methods by mitigating the introduction of noise into the thermodynamic calculations. Additionally, various embodiments described herein can include a practical application of quantum algorithms, such as VQE algorithms, to analyze thermodynamic observables of chemical systems.

FIG. 1 illustrates a block diagram of an example, non-limiting system 100 that can facilitate quantum-based computing of a chemical system's thermodynamic observables. Repetitive description of like elements employed in other embodiments described herein is omitted for sake of brevity. Aspects of systems (e.g., system 100 and the like), apparatuses or processes in various embodiments of the present invention can constitute one or more machine-executable components embodied within one or more machines, e.g., embodied in one or more computer readable mediums (or media) associated with one or more machines. Such components, when executed by the one or more machines, e.g., computers, computing devices, virtual machines, etc. can cause the machines to perform the operations described.

As shown in FIG. 1, the system 100 can comprise one or more servers 102, one or more networks 104, input devices 106, and/or quantum computers 108. The server 102 can comprise computations component 110. The computations component 110 can further comprise communications component 112 and/or optimizer component 114. Also, the server 102 can comprise or otherwise be associated with at least one memory 116. The server 102 can further comprise a system bus 118 that can couple to various components such as, but not limited to, the computations component 110 and associated components, memory 116 and/or a processor 120. While a server 102 is illustrated in FIG. 1, in other embodiments, multiple devices of various types can be associated with or comprise the features shown in FIG. 1. Further, the server 102 can communicate with one or more cloud computing environments.

The one or more networks 104 can comprise wired and wireless networks, including, but not limited to, a cellular network, a wide area network (WAN) (e.g., the Internet) or a local area network (LAN). For example, the server 102 can communicate with the one or more input devices 106 and/or quantum computers 108 (and vice versa) using virtually any desired wired or wireless technology including for example, but not limited to: cellular, WAN, wireless fidelity (Wi-Fi), Wi-Max, WLAN, Bluetooth technology, a combination thereof, and/or the like. Further, although in the embodiment shown the computations component 110 can be provided on the one or more servers 102, it should be appreciated that the architecture of system 100 is not so limited. For example, the computations component 110, or one or more components of computations component 110, can be located at another computer device, such as another server device, a client device, etc.

The one or more input devices 106 can comprise one or more computerized devices, which can include, but are not limited to: personal computers, desktop computers, laptop computers, cellular telephones (e.g., smart phones), computerized tablets (e.g., comprising a processor), smart watches, keyboards, touch screens, mice, a combination thereof, and/or the like. A user of the system 100 can utilize the one or more input devices 106 to input one or more initial quantum Hamiltonians into the system 100, thereby sharing (e.g., via a direct connection and/or via the one or more networks 104) said data with the server 102. For example, the one or more input devices 106 can send data to the communications component 112 (e.g., via a direct connection and/or via the one or more networks 104). Additionally, the one or more input devices 106 can comprise one or more displays that can present one or more outputs generated by the system 100 to a user. For example, the one or more displays can include, but are not limited to: cathode tube display ("CRT"), light-emitting diode display ("LED"), electroluminescent display ("ELD"), plasma display panel ("PDP"), liquid crystal display ("LCD"), organic light-emitting diode display ("OLED"), a combination thereof, and/or the like.

A user of the system 100 can utilize the one or more input devices 106 and/or the one or more networks 104 to input one or more settings and/or commands into the system 100. For example, in the various embodiments described herein, a user of the system 100 can operate and/or manipulate the server 102 and/or associate components via the one or more input devices 106. Additionally, a user of the system 100 can utilize the one or more input devices 106 to display one or more outputs (e.g., displays, data, visualizations, and/or the like) generated by the server 102 and/or associate components. Further, in one or more embodiments, the one or more input devices 106 can be comprised within, and/or operably coupled to, a cloud computing environment.

For example, in various embodiments the one or more input devices 106 can be employed to enter one or more initial quantum Hamiltonians into the system 100 for analysis via one or more VQE algorithms. For example, the initial quantum Hamiltonian can comprise a sum of Pauli matrices and/or can be obtained by applying one or more versions of a Jordan-Wigner encoding. The initial quantum Hamiltonian can characterize the inter-particle interactions of a chemical system, which can be a set of separable, or inseparable, operators that can evolve the wavefunction to a stationary eigenstate (e.g., wherein the eigenvalues of which are the energy). In one or more embodiments, the system 100 can be initialized with the atomic coordinates (e.g., internal or absolute) of one or more given molecules and/or atom types/basis sets, from which the initial quantum Hamiltonian can be derived.

In various embodiments, the one or more quantum computers 108 can comprise quantum hardware devices that can utilize the laws of quantum mechanics (e.g., such as superposition and/or quantum entanglement) to facilitate computational processing (e.g., while satisfying the DiVincenzo criteria). In one or more embodiments, the one or more quantum computers 108 can comprise a quantum data plane, a control processor plane, a control and measurement plane, and/or a qubit technology.

In one or more embodiments, the quantum data plane can include one or more quantum circuits comprising physical qubits, structures to secure the positioning of the qubits, and/or support circuitry. The support circuitry can, for example, facilitate measurement of the qubits' state and/or perform gate operations on the qubits (e.g., for a gate-based system). In some embodiments, the support circuitry can comprise a wiring network that can enable multiple qubits to interact with each other. Further, the wiring network can facilitate the transmission of control signals via a direct electrical connection and/or electromagnetic radiation (e.g., optical, microwave, and/or low-frequency signals). For instance, the support circuitry can comprise one or more superconducting resonators operatively coupled to the one or more qubits. As described herein the term "superconducting" can characterize a material that exhibits superconducting properties at or below a superconducting critical temperature, such as aluminum (e.g., superconducting critical temperature of 1.2 Kelvin) or niobium (e.g., superconducting critical temperature of 9.3 Kelvin). Additionally, one of ordinary skill in the art will recognize that other superconductor materials (e.g., hydride superconductors, such as lithium/magnesium hydride alloys) can be used in the various embodiments described herein.

In one or more embodiments, the control processor plane can identify and/or trigger a Hamiltonian sequence of quantum gate operations and/or measurements, wherein the sequence executes a program (e.g., provided by a host processor, such as server 102, via computations component 110) for implementing a quantum algorithm (e.g., a VQE algorithm). For example, the control processor plane can convert compiled code to commands for the control and measurement plane. In one or more embodiments, the control processor plane can further execute one or more quantum error correction algorithms.

In one or more embodiments, the control and measurement plane can convert digital signals generated by the control processor plane, which can delineate quantum operations to be performed, into analog control signals to perform the operations on the one or more qubits in the quantum data plane. Also, the control and measurement plane can convert one or more analog measurement outputs of the qubits in the data plane to classical binary data that can be shared with other components of the system 100 (e.g., such as the computations component 110, via, for example, the control processor plane).

One of ordinary skill in the art will recognize that a variety of qubit technologies can provide the basis for the one or more qubits of the one or more quantum computers 108. Two exemplary qubit technologies can include trapped ion qubits and/or superconducting qubits. For instance, wherein the quantum computer 108 utilizes trapped ion qubits, the quantum data plane can comprise a plurality of ions serving as qubits and one or more traps that serve to hold the ions in specific locations. Further, the control and measurement plane can include: a laser or microwave source directed at one or more of the ions to affect the ion's quantum state, a laser to cool and/or enable measurement of the ions, and/or one or more photon detectors to measure the state of the ions. In another instance, superconducting qubits (e.g., such as superconducting quantum interference devices "SQUIDs") can be lithographically defined electronic circuits that can be cooled to milli-Kelvin temperatures to exhibit quantized energy levels (e.g., due to quantized states of electronic charge or magnetic flux). Superconducting qubits can be Josephson junction-based, such as transmon qubits and/or the like. Also, superconducting qubits can be compatible with microwave control electronics, and can be utilized with gate-based technology or integrated cryogenic controls. Additional exemplary qubit technologies can include, but are not limited to: photonic qubits, quantum dot qubits, gate-based neutral atom qubits, semiconductor qubits (e.g., optically gated or electrically gated), topological qubits, a combination thereof, and/or the like.

In one or more embodiments, the communications component 112 can receive one or more initial quantum Hamiltonians from the one or more input devices 106 (e.g., via a direct electrical connection and/or through the one or more networks 104) and share the data with the various associate components of the computations component 110. Additionally, the communications component 112 can facilitate the sharing of data between the computations component 110 and the one or more quantum computers 108, and/or vice versa (e.g., via a direct electrical connection and/or through the one or more networks 104).

In various embodiments, the one or more quantum computers 108 can comprise one or more VQE components 122 (e.g., comprised within the control processor plane) that can execute one or more VQE algorithms on the quantum computers 108. In one or more embodiments, the one or more VQE components 122 and the one or more optimizer components 114 can function in combination to execute an iterative VQE algorithm based on the one or more initial quantum Hamiltonians. For example, the one or more VQE components 122 and/or optimizer components 114 can function in combination to execute one or more VQE algorithms that can compute the potential energy surface of one or more molecules of the given chemical system. In one or more embodiments, the one or more VQE components 122 and/or optimizer components 114 can utilize one or more Born-Oppenheimer approximations to determine the BOPES of one or more molecules of the chemical system, wherein the BOPES can characterize the electronic energy as a function of bond length of the given molecule.

As used herein the term "variational quantum eigensolver ("VQE") algorithm" or "VQE algorithms" can refer to one or more hybrid quantum-classical computing algorithms that can share computational work between classical computing hardware (e.g., the one or more servers 102 via the computations component 110 and/or the optimizer component 114) and quantum computing hardware (e.g., the one or more quantum computers 108 via the VQE component 122) to reduce the long coherence times required by all-quantum phase estimation algorithms. A VQE algorithm can be initialized with one or more assumptions regarding the form of a target wavefunction. Based on the one or more assumptions, an ansatz with one or more tunable parameters can be constructed and a quantum circuit capable of producing the ansatz can be designed. Throughout execution of the VQE algorithm, the ansatz parameters can be variationally adjusted to minimize the expectation value of resulting Hamiltonian matrix. Classical computing hardware (e.g., the one or more servers 102 via the computations component 110 and/or the optimizer component 114) can precompute one or more terms of the Hamiltonian matrix and/or update the parameters during optimization of a quantum circuit. The quantum hardware (e.g., the one or more quantum computers 108 via the VQE component 122) can prepare a quantum state (e.g., defined by the current iteration's set of ansatz parameter values) and/or perform measurements of various interaction terms in the Hamiltonian matrix. The state preparation can be repeated over multiple iterations until each individual operator has been measured enough times to derive sufficient statistical data. Additionally, the efficiency of VQE algorithms can be improved by using particle-hole mapping of the quantum Hamiltonian to produce improved starting points for the trail wavefunction. Further, methods to reduce the number of qubits required for electronic structure calculations (e.g., such as qubit tapering) can eliminate redundant degrees of freedom in the Hamiltonian.

In various embodiments, the VQE component 122 can execute one or more VQE algorithms that can minimize the expectation value $E_H(\psi) = \langle\psi|H|\psi\rangle$, wherein H is a given Hamiltonian and $\psi$ is a quantum state from the domain D of $E_H$. Mathematically, $E_H(\psi)$ can be the Rayleigh quotient for the Hermitian matrix $H \in \mathbb{C}^{2^n \times 2^n}$ and the unit vector $\psi \in D \subseteq \mathbb{C}^{2^n}$ and, provided that the eigenvector $\phi_0$ corresponding to the smallest eigenvalue $\lambda_0$ of H is in D, $\lambda_0$ can be characterized by Equation 1 below.

$$\min_{\psi \in D} E_H(\psi) = \min_{\psi \in D} \langle\psi|H|\psi\rangle = \langle\phi_0|H|\phi_0\rangle = \lambda_0 \qquad (1)$$

The VQE component 122 can perform the expectation value evaluations on the quantum computer 108 via the VQE algorithm in conjunction with an optimization algorithm executed by the optimizer component 114 to minimize $E_H$. Further, the optimization algorithm can be rendered tractable by classical computing techniques through the reduction of the dimension of D using a parameterized quantum circuit $U: \mathbb{R}^m \to \mathbb{C}^{2^n \times 2^n}$ as the ansatz, which can map the low-dimensional space $\mathbb{R}^m$ to unitary operators $U(\theta)$. The VQE algorithm can thus become a classical computing minimization of the quantum-evaluated function $f: \mathbb{R}^m \to \mathbb{C}$ given by Equation 2 below.

$$f(\theta) = \langle U(\theta)\psi_0|H|U(\theta)\psi_0\rangle \qquad (2)$$

Wherein $|\psi_0\rangle$ can be an initial state, which can then be perturbed by the parameterized circuit U. For example, it can be the state $|0\rangle$, or some other quantum state that can be efficiently constructed by a state preparation circuit $U_0$, as characterized by Equation 3 below.

$$|\psi_0\rangle = U_0|0\rangle \qquad (3)$$

For example, in various embodiments the variational-form of the ansatz can be given by single-qubit $R_y$ rotations interleaved by a series of two-qubit entangling gates, and the initial state can be the ground state of the Hartree-Fock Hamiltonian.

In one or more embodiments, the VQE component 122 can further implement one or more qubit tapering procedures (e.g., derived by the VQE component 122 and/or the computations component 110, entered via the one or more input devices 106, and/or received via the communications component 112). Molecular electronic Hamiltonians conserve the number of particles with fixed spin orientations. This implies that the problem can be effectively described in a subspace of the full Hilbert space with a defined number of spin-up and spin-down particles. This reduction in the required Hilbert space can be a result of the spin-particle conservation symmetry of the Hamiltonian. Apart from these symmetries, certain molecules also exhibit spatial or geometric symmetries under the operations described by reflections or rotations. On mapping the second quantized representation of the fermionic molecular Hamiltonian to a qubit Hamiltonian by using the well-known encodings like Jordan-Wigner or its variants, such as parity encoding and binary tree encodings, the symmetries corresponding to spin-particle number conservation and geometric symmetries can be captured by the $\mathbb{Z}_2$ symmetries of the qubit Hamiltonian. The qubit tapering procedure can include a systematic way of finding multiple $\mathbb{Z}_2$ symmetries in the qubit Hamiltonian and transforming this Hamiltonian such that one qubit for each $\mathbb{Z}_2$ symmetry can be removed from the description. Further, the energy spectrum obtained from the original Hamiltonian and the tapered Hamiltonian can be identical. The one or more qubit tapering procedures can reduce the qubit count and heuristic ansatz needed to execute the VQE algorithm.

In one or more embodiments, the VQE component 122 can further implement one or more particle hole mapping procedures (e.g., derived by the VQE component 122 and/or the computations component 110, entered via the one or more input devices 106, and/or received via the communications component 112). Variational quantum algorithms include the preparation of suitable trial wavefunctions. The particle/hole transformation in this context can provide improved reference trial wavefunctions and/or realization of the VQE algorithm. The one or more particle hole mapping procedures can be based on transforming the electronic Hamiltonian in the second quantization into the particle/hole picture, where the state of the molecular system of interest can be parametrized to efficiently explore the sector of the molecular Fock space that contains the desired solution. The electronic Hamiltonian in the particle/hole picture can be characterized by Equation 4 below.

$$H^{p/h} = E_{HF} \Sigma_{rs} <r|F|s> N_b [a_r^\dagger a_s] + \tfrac{1}{2} \Sigma_{srtu} <rs|g|tu> N_b [a_r^\dagger a_s^\dagger a_u a_t] \qquad (4)$$

Wherein $E_{HF} = \Sigma_i <i|h|i> + \tfrac{1}{2} \Sigma_{ij}(<ij|g|ij> - <ij|g|ji>)$, and $<r|F|s>$ being the Fock matrix $<r|F|s> = <r|h|s> + \Sigma_i (<ri|g|si> - <ri|g|is>)$. Also, the normal ordering operator $N_b$ acts on the particle/hole operators.

For instance, the computations component 110 can calculate the HF orbitals and/or store the required matrix elements $<i|h|i>$ and/or $<ij|g|ji>$ (e.g., stored into the memory 116). Next, the computations component 110 can execute a Jordan-Wigner transformation to map the fermionic Hamiltonian to the qubit Hamiltonian. Thereupon, the computations component 110 (e.g., via the optimizer component 114) can generate the trail wavefunctions starting from the HF ground state. The VQE component 122 can utilize the quantum computer 108 to calculate the expectation value of $H^{p/h}$. The optimizer component 114 can perform an energy optimization using an optimization algorithm and return the updates to repeat the process until convergence is achieved.

In various embodiments, the optimizer component 114 can execute an optimization algorithm to facilitate the variation of the ansatz parameters during execution of the VQE algorithm on the one or more quantum computers 108 (e.g., via the VQE component 122). In one or more embodiments, the optimizer component 114 can comprise an AQGD optimizer that can implement a stochastic gradient descent ("SGD") method with momentum via the optimization algorithm. For example, as characterized by Equations 5-6 below:

$$m^k = (1-\mu) g^k + \mu m^{k-1}, \qquad (5)$$

$$\theta^{(k+1)} = \theta^k - \gamma^k m^k \qquad (6)$$

Wherein $m^0 = 0, \mu \in [0,1)$ can be the momentum parameter, $\gamma^k$ can be the step length, and/or $g^k$ can be the current gradient estimate. For instance, $\mu = 0$ can correspond to a standard SGD.

In various embodiments, the optimizer component 114 can implement the bootstrapping, resampling, customizable step length scheduling, and/or adaptive termination computation processes to enable an efficient and/or robust calculation of the dissociation curve. For instance, the optimization algorithm can obtain gradients using the parameter shift rule. Along with evaluation of the objective and/or energy estimate at the current parameter point, the cost per iteration of the SGD method can be characterized as 2np+1 energy evaluations, wherein np can be the number of ansatz parameters. This cost can be justified as "full" gradient information and can lead to quicker decrease of the energy. Step lengths can decrease to zero with an asymptotic behavior like 1/k, wherein k can be the iteration count. The specific step length schedule can use a step length equal to 1 for a first set of iterations w (e.g., 10 iterations), then decrease it by setting step length to 1/(k−w), for k>w (e.g., 1/(k−10), for k>10).

Further, the optimizer component 114 can use an adaptive termination condition. For example, a window of energy estimates from previous iterations can be maintained, and the method can monitor convergence to a stationary point, or a region near a stationary point, when a change in the windowed average of objective values is less than a defined tolerance. For instance, the tolerance can be equal to 0.001 Hartree. This is a heuristic, with no guarantee of convergence in the presence of noise; however, using a window length of at least four iterations can exhibit a robust performance of the optimization algorithm (e.g., the optimization method avoids performing all the allocated iterations).

Wherein the VQE algorithm terminates, the ansatz parameters are available and can correspond to a wavefunction whose energy can be estimated by the VQE component 122. In various embodiments, the optimizer component 114 can evaluate an estimate as part of the optimization procedure; however, depending on the current internuclear distance, the estimate may not be sufficiently accurate. Consequently, the optimizer component 114 can use the individual circuit shots to estimate a variance $\sigma^2$ for the energy estimate. The optimizer component 114 can further repeat the energy estimation N times and take the average, wherein the new estimator can have variance $\sigma^2/N$. Thereby, the optimizer component 114 can ensure that the standard deviation is less than or equal to $\in$ by taking $N = \lceil \sigma^2/\in^2 \rceil$. Assuming normality of this estimator, this can give a high probability (e.g., greater than 68%) that the energy estimate is within $\in$ of the real value. Since the Hamiltonian, and thus the estimator and its variance, can depend on the internuclear distance, so can N, and so the number of repeated samples can adapt depending on the location in the dissociation curve.

For example, the Hamiltonian of interest H can be implemented as $H = \Sigma_{\alpha=1}^{n_0} h_\alpha P_\alpha$; thus the true energy $<H>$ can be estimated by Equation 7 below.

$$<\hat{H}> = \Sigma_{\alpha=1}^{n_0} h_\alpha <\hat{P}_\alpha> \qquad (7)$$

Wherein $<\hat{P}_\alpha>$ can be an estimator of the mean value of the α-th operator defined in accordance with Equation 8 below.

$$<\hat{P}_\alpha>=1/n_s\Sigma_{i=1}^{n_s}X_{i,\alpha} \quad (8)$$

Wherein $n_s$ can be the number of circuit evaluations, and $X_{i,\alpha}$ is the measurement outcome of the i-th circuit evaluation. Since $\{X_{i,\alpha}\}$ can be independent identically distributed ("i.i.d.") random variables, the central limit theorem can be applied, and since $n_s$ can be an order of magnitude of $10^3$ to $10^4$, the assumption that $<\hat{P}_\alpha>$ follows a normal distribution can be reasonable. Taking a linear combination of $<\hat{P}_\alpha>$ to yield $<\hat{H}>$ can preserve the gaussian nature, as does further averaging over N independent trials $\{<\hat{H}>_j; j=1, \ldots, N\}$ to yield the ultimate estimator $\hat{E} \equiv 1/N\Sigma_{j=1}^N<\hat{H}>_j$. The estimator of the variance of $<\hat{H}>$ is $\sigma^2$, and so the optimizer component 114 can take $\sigma^2/N$ as (an estimator of) the variance of $\hat{E}$. The variance can take into account correlations between estimators for different operators, since the same set of measurement outcomes can be used to evaluate $<\hat{P}_\alpha>$ and/or $<\hat{P}_\beta>$ ($\alpha \neq \beta$). Additionally, even without assuming normality, the optimizer component 114 can utilize Chebyshev's inequality; wherein the energy estimator $\hat{E}$ can be a random variable with mean $<H>$ with a variance of $\sigma^2/N$. For example, Chebyshev's inequality can render Equation 9 below, for any real $\eta>0$.

$$P(|\hat{E}-<H>|\geq\eta\Gamma/\sqrt{N})\leq 1/\eta^2 \quad (9)$$

Taking $\eta>1$ and $N=\eta^2\sigma^2/E^2$ can guarantee that there is a non-zero probability that the estimator is within E of the true mean.

Further, the VQE algorithm can be executed by the VQE component 122 and/or optimizer component 114 to develop a full dissociation curve of the given chemical system, wherein the energy surfaces at two nearby internuclear distances can be similar. Thereby, the optimizer component 114 can render the overall dissociation curve calculation more efficient and/or robust by bootstrapping the classical optimization at each point along the dissociation curve. For instance, since the ansatz can begin with the Hartree-Fock state, which can be a reasonable approximation of the state at smaller internuclear distances, the optimizer component 114 can initiate the calculation of the dissociation curve at the smallest internuclear distance of interest. The VQE algorithm can terminate to output a set of optimal ansatz parameters. The optimizer component 114 can analyze the next smallest internuclear distance and/or use the optimal ansatz parameters as start for the initial point utilized in the SGD method. In one or more embodiments, these parameter values can be nearly optimal for the new point on the dissociation curve. Combined with the adaptive termination conditions, the optimizer component 114 can save multiple iterations of the SGD method. After calculating the whole dissociation curve, the procedure can be repeated, starting again from the smallest internuclear distance with new random initial ansatz parameters. With three such independent passes, the optimizer component 114 can dismiss outliers at any point along the dissociation curve.

Figure 2:
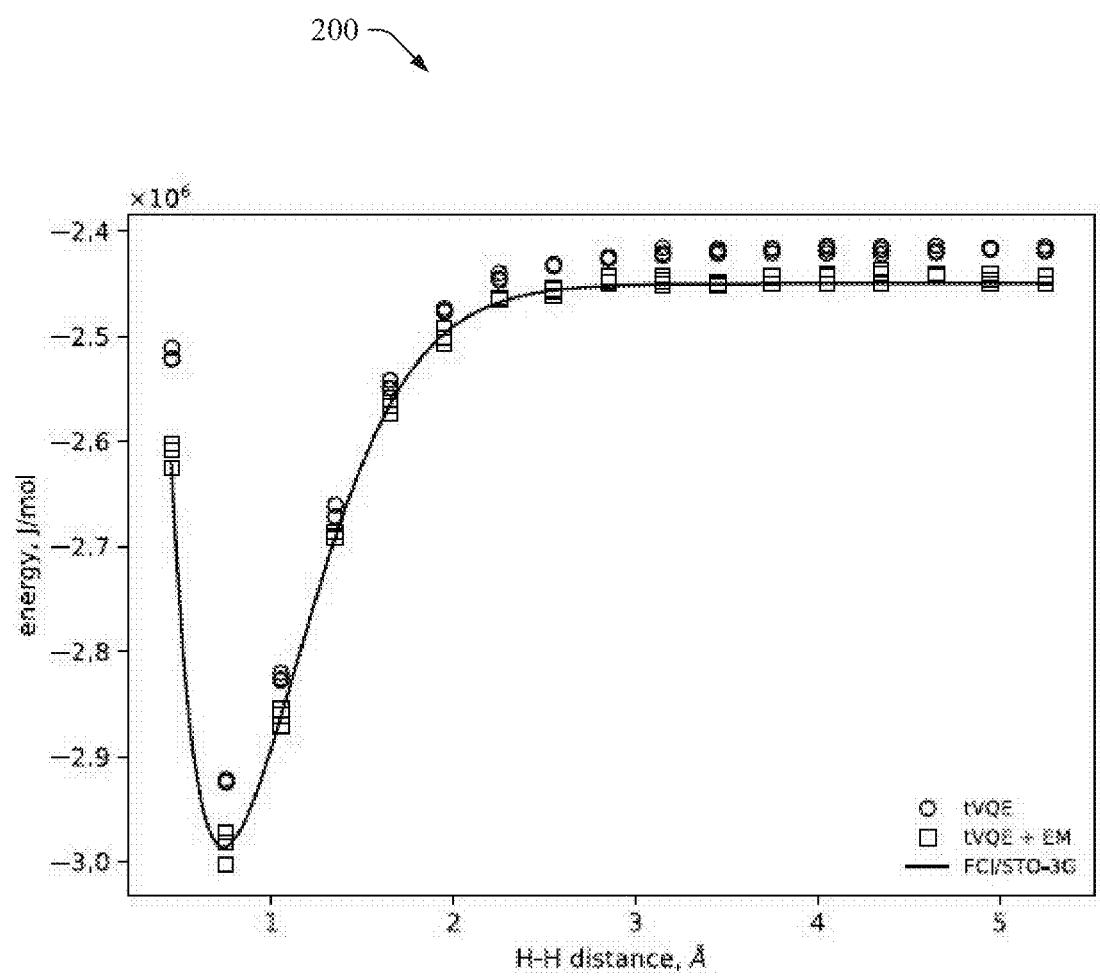
FIG. 2 illustrates a diagram of an example, non-limiting dissociation curve that can be generated via execution of one or more VQE algorithms to facilitate computing thermodynamic observables in accordance with one or more embodiments described herein.

FIG. 2 illustrates a diagram of an example, non-limiting dissociation curve 200 that can be computed by the system 100 (e.g., via the VQE component 122 and/or optimizer component 144) in accordance with one or more embodiments described herein. Repetitive description of like elements employed in other embodiments described herein is omitted for sake of brevity. In various embodiments, the VQE component 122 can function in combination with the optimizer component 114 to execute the VQE algorithm and compute the BOPES of the one or more given molecules (e.g., a hydrogen molecule, as depicted in FIG. 2), wherein the BOPES can characterize an electronic energy as a function of bond length. Thereby, the VQE component 122 and optimizer component 114 can generate a dissociation curve for the one or more given molecules, such as the exemplary dissociation curve 200 regarding a hydrogen molecule. To derive the exemplary dissociation curve 200, the STO-3G basis set, with two spin orbitals, the minimum to describe the hydrogen molecule, was used with the VQE algorithm. This can equate to performing a classical FCI/STO-3G calculation since the VQE algorithm can find the lowest eigenvalue of the complete Hamiltonian, which can be the full configuration interaction ("FCI") solution to the electronic Schrodinger equation. Wherein the quantum computer 108 calculation (e.g., with the STO-3G basis set) is accurate, the results can coincide with the FCI/STO-3G classical calculation.

FIG. 2 shows the potential energy surface for the hydrogen molecule ($H_2$) computed using the quantum computer 108 with qubit tapering and with or without measurement error mitigation (e.g., "tVQE+EM" and "tVQE", respectively). The solid line shows the reference FCI/STO-3G calculation. FIG. 2 illustrates that execution of the VQE algorithm with qubit tapering, particle-hole transformation, an AQGD optimizer, and/or measurement error mitigation (e.g., "VQE/STO-3G"), as described in the various embodiments herein, can enable the quantum calculation to reproduce the solution. However, unlike the calculation on the classical computer, there is noise that remains in the VQE calculation (e.g., as evidenced by the scatter in the three replicates at each bond length). Further, despite good agreement between the VQE/STO-3G calculation and the FCI/STO-3G calculation, the noise in the quantum computer 108 can make a finite difference-based analysis problematic.

Figure 3:
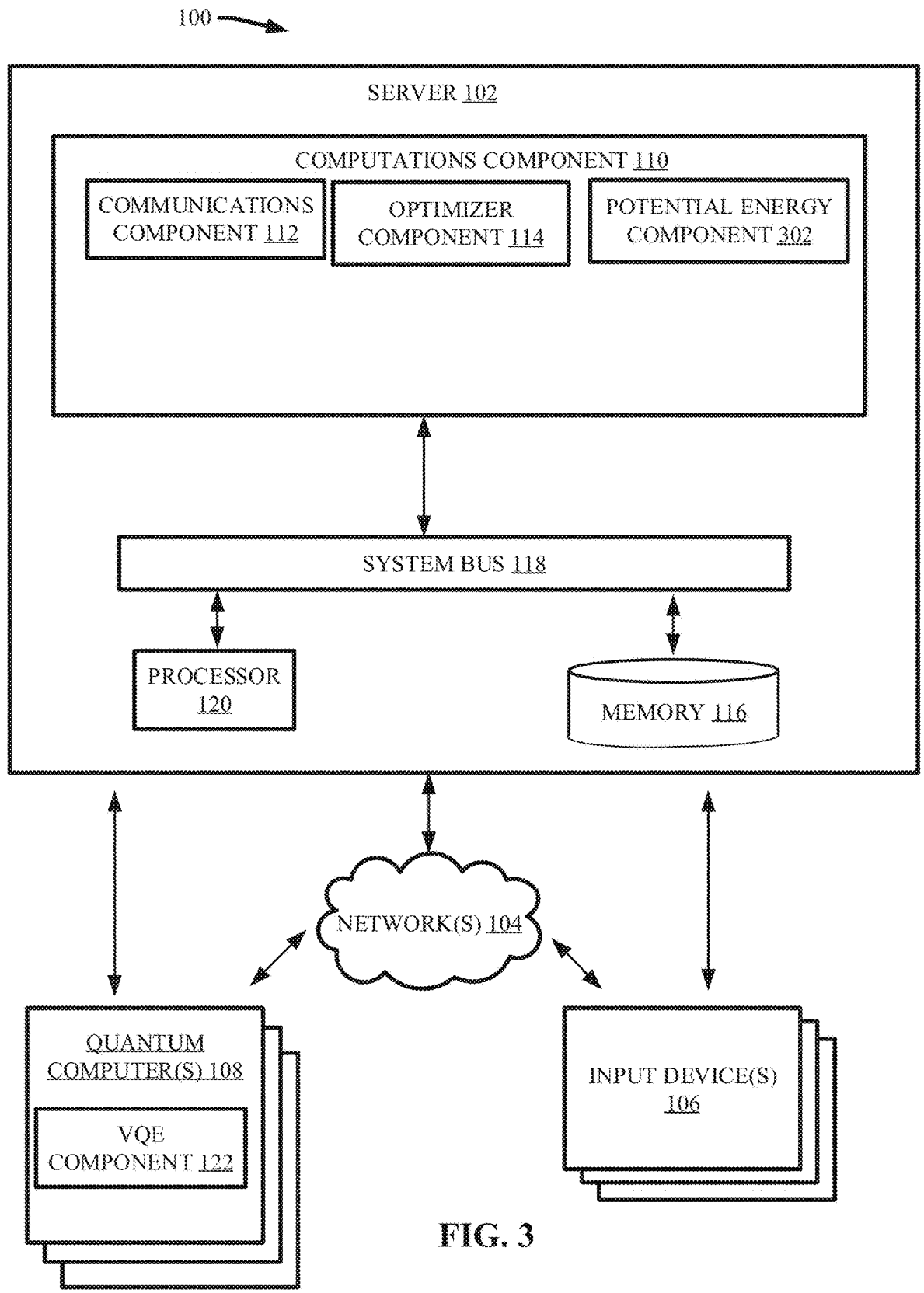
FIG. 3 illustrates a diagram of an example, non-limiting system that can utilize a parameterized potential energy function to mitigate noise generated by a quantum device during execution of a VQE algorithm in accordance with one or more embodiments described herein.

FIG. 3 illustrates a diagram of the example, non-limiting system 100 further comprising potential energy component 302 in accordance with one or more embodiments described herein. Repetitive description of like elements employed in other embodiments described herein is omitted for sake of brevity. In various embodiments, the potential energy component 302 can fit one or more molecular potential energy functions to the dissociation curve generated by the optimizer component 114 and/or VQE component 122 via execution of the VQE algorithm. For example, the potential energy component 302 can use a potential energy loss function as a parameterized potential energy surface so that a large number of VQE/STO-3G calculations across a wide range of bond lengths can be used to fit the parameters; thereby reducing the effect of noise from any one single point energy.

In one or more embodiments, the one or more potential energy functions can characterize interatomic interactions of a given molecule of the chemical system. For example, the one or more potential energy functions can approximate the vibrational structure of the molecule. Example potential energy functions that can be fitted to the dissociation curve (e.g., fitted to the BOPES determined via the VQE algorithm) can include, but are not limited to: a Morse potential function, a harmonic potential function, generalized Morse potential function, Lennard Jones functions, parabolic functions, cubic spline functions, harmonic displacement from an equilibrium angle and/or spline, sine series functions, cosine series functions, Fourier series functions, a combination thereof, and/or the like. For instance, in one or more embodiments the potential energy component 302 can fit a Morse potential energy function to the dissociation curve of the VQE algorithm. The Morse potential energy function can be characterized by Equation 10 below, wherein V(r) can be the potential energy as a function of the interatomic distance r. Further, the described parameters with regards to the Morse Potential can be potential energy well depth $D_e$, the width $\alpha$ of the potential energy well (e.g., related to the force constant between the atoms, and/or the equilibrium bond length $r_0$.

$$V(r) = D_e(1 + e^{-\alpha(r-r_0)})^2 \tag{10}$$

In addition to the mitigation of noise, fitting the potential energy function can also have several other advantages. For example, parameterizing the potential energy function can account for the uneven spacing of vibrational energy levels and/or the anharmonicity present in given molecules.

Thereby, the potential energy component 302 can parameterize the molecular potential energy function based on the dissociation curve to mitigate noise inherent to the quantum computer 108. For example, the one or more quantum computers 108 can comprise one or more noisy intermediate-scale quantum ("NISQ") devices, wherein noise can be inherent in single-point energy calculations.

Figure 4:
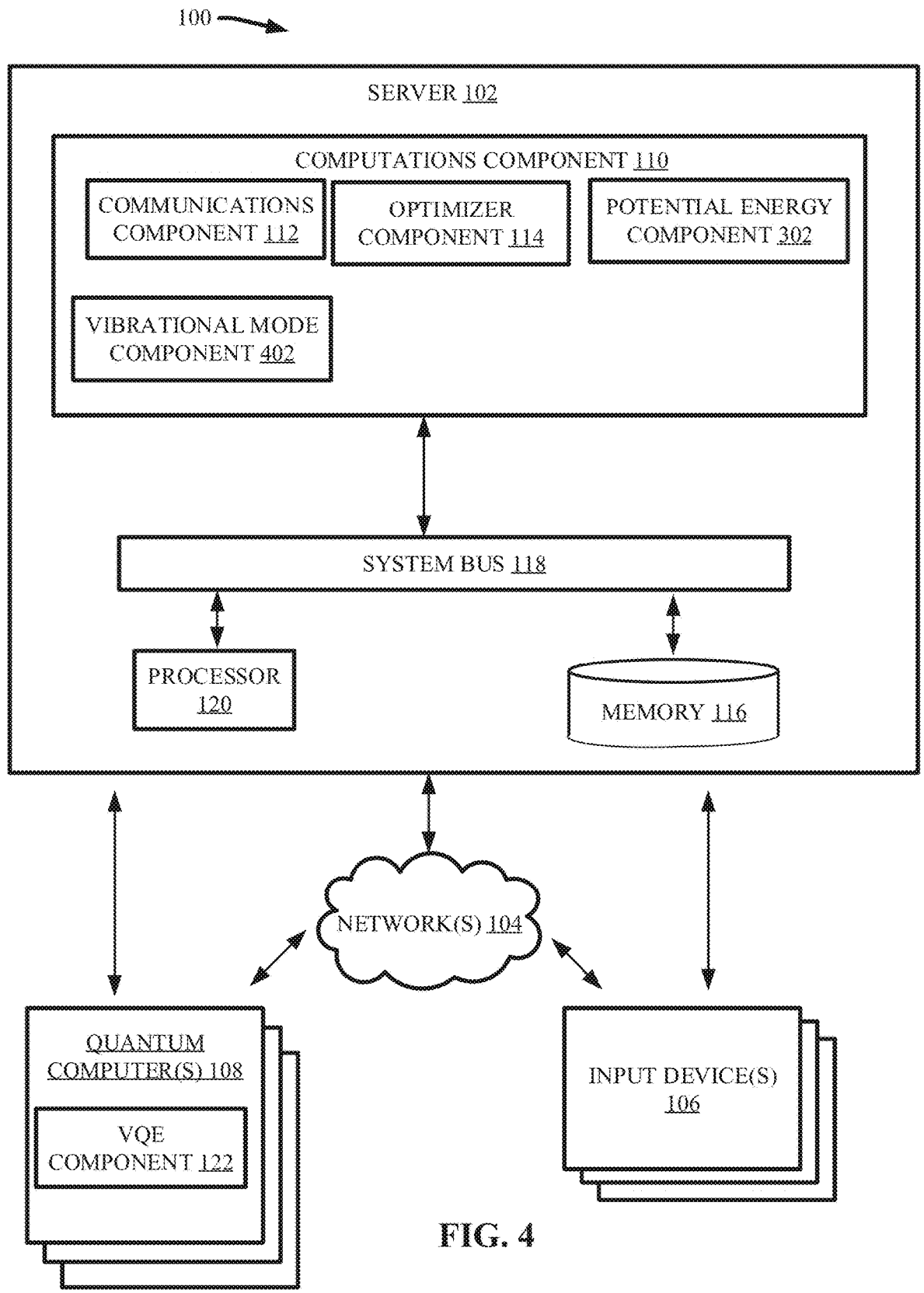
FIG. 4 illustrates a block diagram of an example, non-limiting system that can compute one or more intramolecular vibrational modes based on a parameterized potential energy function in accordance with one or more embodiments described herein.

FIG. 4 illustrates a diagram of the example, non-limiting system 100 further comprising vibrational mode component 402 in accordance with one or more embodiments described herein. Repetitive description of like elements employed in other embodiments described herein is omitted for sake of brevity. In various embodiments, the vibrational mode component 402 can compute one or more intramolecular vibrational modes of the molecule based on the fitted BOPES (e.g., based on the potential energy surface fitted with the potential energy function). The parameterized potential energy functions (e.g., fitted Morse potential) can provide analytical solutions for the vibrational energy levels of the one or more given molecules For example, the vibrational mode component 402 can compute the one or more vibrational modes in accordance with Equation 11 below.

$$\epsilon_n = h\nu_0\left(n + \frac{1}{2}\right) - \frac{\left[h\nu_0\left(n + \frac{1}{2}\right)\right]^2}{4D_e}, n = 0, 1, 2\ldots, n_{max} \tag{11}$$

Wherein $\epsilon_n$ can represent the vibrational energy at an energy level n, h can be Planck's constant, $\alpha$ and $D_e$ can be parameters from the potential energy function (e.g., the Morse potential). Further, $\nu_0$ can be fundamental vibrational frequency, and can be related to the reduced mass $m_R$ and the parameters of the potential energy function (e.g., the Morse potential) in accordance with Equation 12 below.

$$\nu_0 = \frac{a}{2\pi}\sqrt{\frac{2D_e}{m_R}} \tag{12}$$

The summation in the energy levels can be computed by the vibrational mode component 402 until the dissociation energy $E_{diss} = D_e - \epsilon_{n,(n=0)}$ is reached. Therefore, the maximum value of n can be characterized by Equation 13 below.

$$n_{max} = \left\lfloor \frac{2D_e - h\nu_0}{h\nu_0} \right\rfloor \tag{13}$$

Wherein $\lfloor \bullet \rfloor$ can be the largest integer smaller than the argument.

Figure 5:
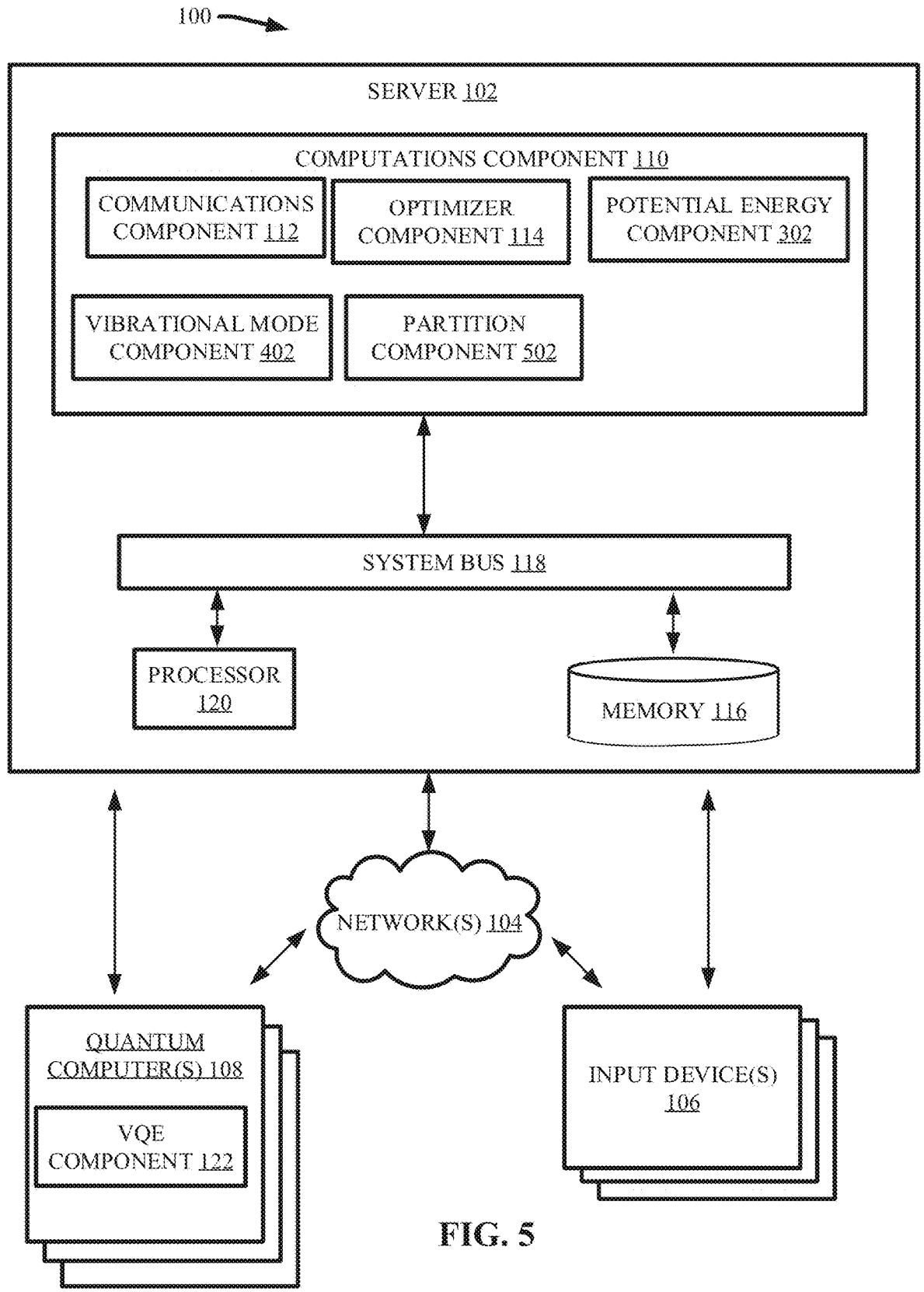
FIG. 5 illustrates a block diagram of an example, non-limiting system that can determine one or more partition functions base on vibrational modes of a molecule in accordance with one or more embodiments described herein.

FIG. 5 illustrates a diagram of the example, non-limiting system 100 further comprising partition component 502 in accordance with one or more embodiments described herein. Repetitive description of like elements employed in other embodiments described herein is omitted for sake of brevity. In various embodiments, the partition component 502 can compute one or more partition functions (e.g., vibrational partition functions) based on the one or more intramolecular vibrational modes.

The partition function can be a dimensionless function describing the state of a thermodynamic ensemble and can be the product of contributions from translational, rotational, vibrational, electronic, and/or nuclear degrees of freedom in accordance with Equation 14 below.

$$q(V,T) = q_{translation} q_{rotation} q_{vibrational} q_{electronic} q_{nuclear} \tag{14}$$

The partition function for the chemical system Q(N,V,T) comprising a plurality of molecules can be computed from the partition function of the given molecules by $Q(N,V,T) = q(V,T)^N/N!$. In one or more embodiments, the electronic and nuclear parts of the molecular partition function can be assumed to be unity wherein nuclear and/or electronic excited states are not accessible for the chemical system at a defined temperature range. Further, the translational partition function can be computed in accordance with Equation 15 below.

$$q_{translation} = \left(\frac{2\pi m k_B T}{h^2}\right)^{3/2} V \tag{15}$$

Wherein the volume V can be obtained from the ideal gas law.

In one or more embodiments, the partition component 502 can compute the one or more partition functions, such as vibrational partition functions, based on the Boltzmann summation of the vibrational energy level computed by the vibrational mode component 402 (e.g., with regards to the Morse Potential) in accordance with Equation 16 below.

$$q_{vibrational} = \sum_{n}^{n_{max}} e^{-\epsilon_n/k_B T} \tag{16}$$

Additionally, the partition component 502 can compute the rotational partition. To exemplify the rotational partition computation, the hydrogen deuteride, a heteronuclear diatomic molecule, can be considered in accordance with Equation 17 below.

$$q_{rotational}^{equilib}(T) = \sum_{J=0}^{J_{max}} (2J+1) e^{-\Theta_r J(J+1)/T} \tag{17}$$

Wherein J can be the rotational mode (e.g., an integer), and the rotational temperature $\Theta_r$ can be defined in accordance with Equation 18 below.

$$\Theta_r = \frac{\hbar^2}{2Ik_B} \tag{18}$$

Wherein the energy of each rotational mode $\epsilon_{rot}$ can be characterized by Equation 19 below.

$$\epsilon_{rot} = \frac{\hbar^2}{2I}J(J+1) \tag{19}$$

Further, the partition component 502 can compute the maximum value for J by limiting the rotational energy level to be less than the dissociation energy in accordance with Equation 20 below.

$$J_{max} = \left\lfloor \frac{\sqrt{\hbar^2 + 8\epsilon_{rot}I} - \hbar}{2\hbar} \right\rfloor, \epsilon_{rot} = E_{diss} \tag{20}$$

In one or more embodiments, the partition component 502 can compute the rotational partition function for one or more homonuclear diatomic molecules. Since each nucleus of a homonuclear diatomic molecule is an identical particle, if the nuclei are interchanged, the total wavefunction must be symmetric for bosons (e.g., integer nuclear spin) or anti-symmetric for fermions (e.g., half-integer nuclear spin). For example, hydrogen has half-integer nuclear spin (e.g., deuterium has integer nuclear spin) so the nuclei can have parallel spins or opposite spins, called ortho-H$_2$ and para-H$_2$, respectively. To maintain the correct anti-symmetry of the wavefunction for both types of H$_2$, the rotational modes that are even can couple to opposite nuclear spins (e.g., para-H$_2$), and odd modes can couple to parallel nuclear spins (e.g., ortho-H$_2$). The sum of these two terms can be the partition function for the equilibrium mixture of ortho-H$_2$ and para-H$_2$ in accordance with Equation 21 below, wherein I can be the nuclear spin.

$$q_{rot-nuc}^{equilib-H_2}(T) = q_{rot-nuc}^{para-H_2}(T) + q_{rot-nuc}^{ortho-H_2}(T) \tag{21}$$

$$= I(2I+1)\sum_{Jeven}^{Jmax}(2J+1)e^{-\frac{\theta_r J(J+1)}{T}} +$$

$$(I+1)(2I+1)\sum_{Jodd}^{Jmax}(2J+1)e^{-\frac{\theta_r J(J+1)}{T}} =$$

$$1\sum_{Jeven}^{Jmax}(2J+1)e^{-\frac{\theta_r J(J+1)}{T}} + 3\sum_{Jodd}^{Jmax}(2J+1)e^{-\frac{\theta_r J(J+1)}{T}}$$

Further, the partition function for a deuterium molecule can be computed in accordance with Equation 22 below, wherein rotational modes that are odd can couple to opposite nuclear spins (e.g., para-D$_2$) and even modes can couple to parallel nuclear spins (e.g., ortho-D$_2$).

$$q_{rot-nuc,I=integer}^{equilib}(T) = \tag{22}$$

$$I(2I+1)\sum_{Jodd}^{Jmax}(2J+1)e^{-\frac{\theta_r J(J+1)}{T}} + (I+1)(2I+1)\sum_{Jeven}^{Jmax}(2J+1)e^{-\frac{\theta_r J(J+1)}{T}}$$

A consequence of the functional form of the rotational partition function for homonuclear diatomic molecules can be that the ratio of ortho-H$_2$:para-H$_2$ approaches 3:1 as temperature increases, in accordance with Equation 23 below.

$$x_{para-H_2} = \frac{q_{rot-nuc}^{para-H_2}(T)}{q_{rot-nuc}^{equlib-H_2}(T)} \tag{23}$$

Wherein $x_{para-H_2}$ can be the mass fraction of para-H$_2$. This constant 3:1 ratio (e.g., at higher temperatures) can be referred to as normal-H$_2$ and can have a partition function in accordance with Equation 24 below.

$$q_{rot-nuc}^{norm-H_2}(T) = (q_{even})^{xpara}(q_{odd})^{xortho} \tag{24}$$

Figure 6:
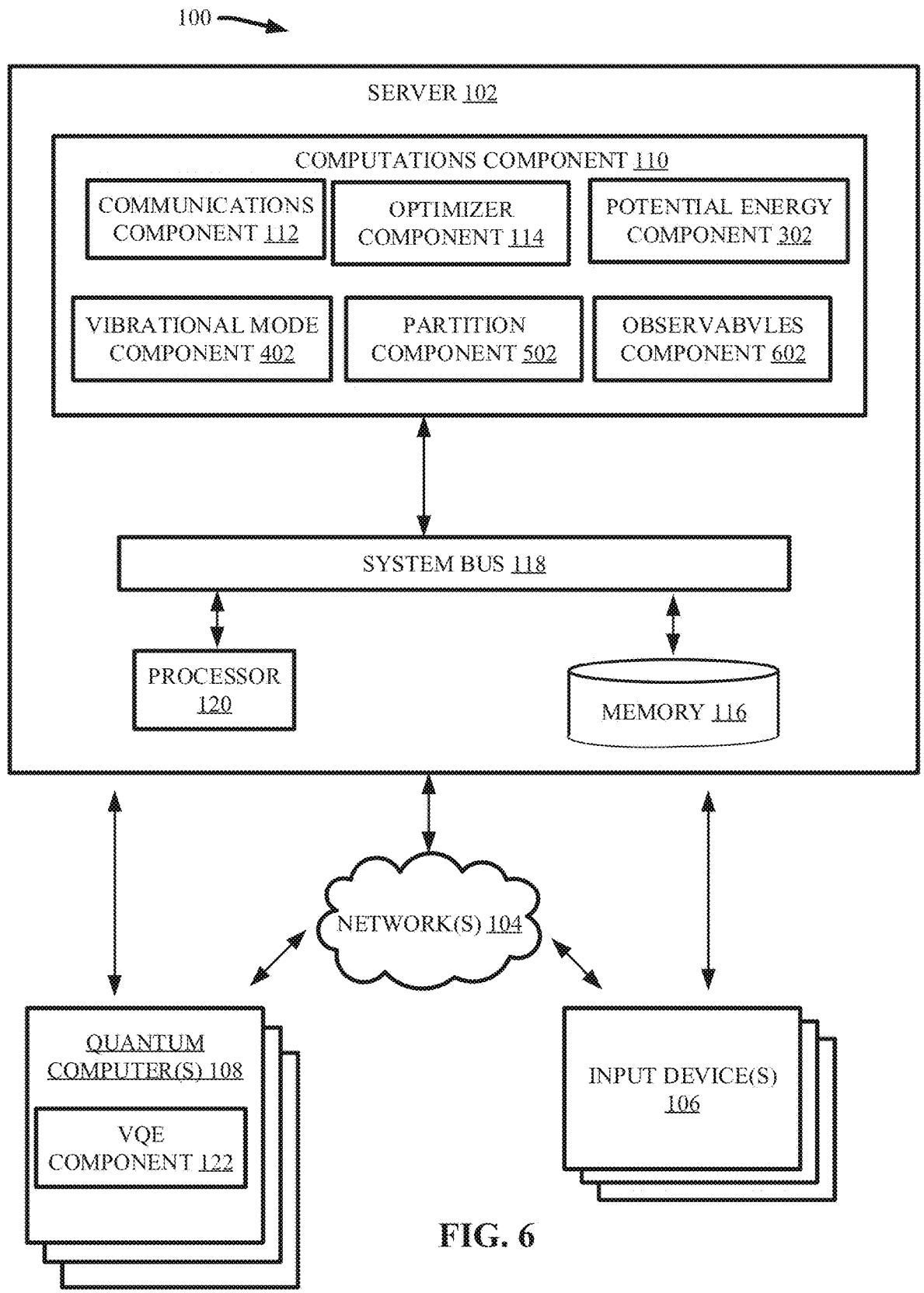
FIG. 6 illustrates a block diagram of an example, non-limiting system that can compute one or more thermodynamic observables of a chemical system based on the one or more partition functions in accordance with one or more embodiments described herein.

FIG. 6 illustrates a diagram of the example, non-limiting system 100 further comprising observables component 602 in accordance with one or more embodiments described herein. Repetitive description of like elements employed in other embodiments described herein is omitted for sake of brevity. In various embodiments, the observables component 602 can compute one or more thermodynamic observables of the molecule and/or chemical system based on the one or more computed partition functions.

In one or more embodiments, the observables component 602 can compute the entropy S, internal energy U, heat capacity C, and/or enthalpy H of the given molecule. Additionally, the observables component 602 can compute the Gibbs free energy G, change in Gibbs free energy per mole of reaction $\Delta G_{rxn}$, constant volume heat capacity, constant pressure heat capacity, Helmholtz free energy, reaction rate, and/or reaction equilibrium constant $K_{eq}$ of the chemical system. For example, the observables component 602 can compute one or more of the thermodynamic observables based on the partition function (e.g., the vibrational and/or rotational partition function) in accordance with Equations 25-33 below.

$$\frac{\partial Q}{\partial \beta} = -\sum_v E_v \exp(-\beta E_v) \tag{25}$$

$$\langle E \rangle = U = -\frac{1}{Q}\frac{\partial Q}{\partial \beta} = -\frac{\partial \ln Q}{\partial \beta}, \beta = \frac{1}{k_b T} \tag{26}$$

$$U = k_b T^2 \frac{\partial \ln Q}{\partial T}\bigg|_{N,V} \tag{27}$$

$$S = \frac{\partial}{\partial T}(k_b T \ln Q) = \frac{\partial A}{\partial T} \tag{28}$$

$$A = U - TS = -k_b T \ln Q \tag{29}$$

$$H = U + N_A k_b T \tag{30}$$

$$G = H - TS \tag{31}$$

$$C_v = \frac{\partial U}{\partial T}\bigg|_{N,V} \tag{32}$$

$$K_{eq} = e^{\frac{\Delta G_{rxn}}{RT}} \tag{33}$$

Wherein N can represent the number of particles, V can represent the volume and/or Q can represent the system partition function.

Figure 7:
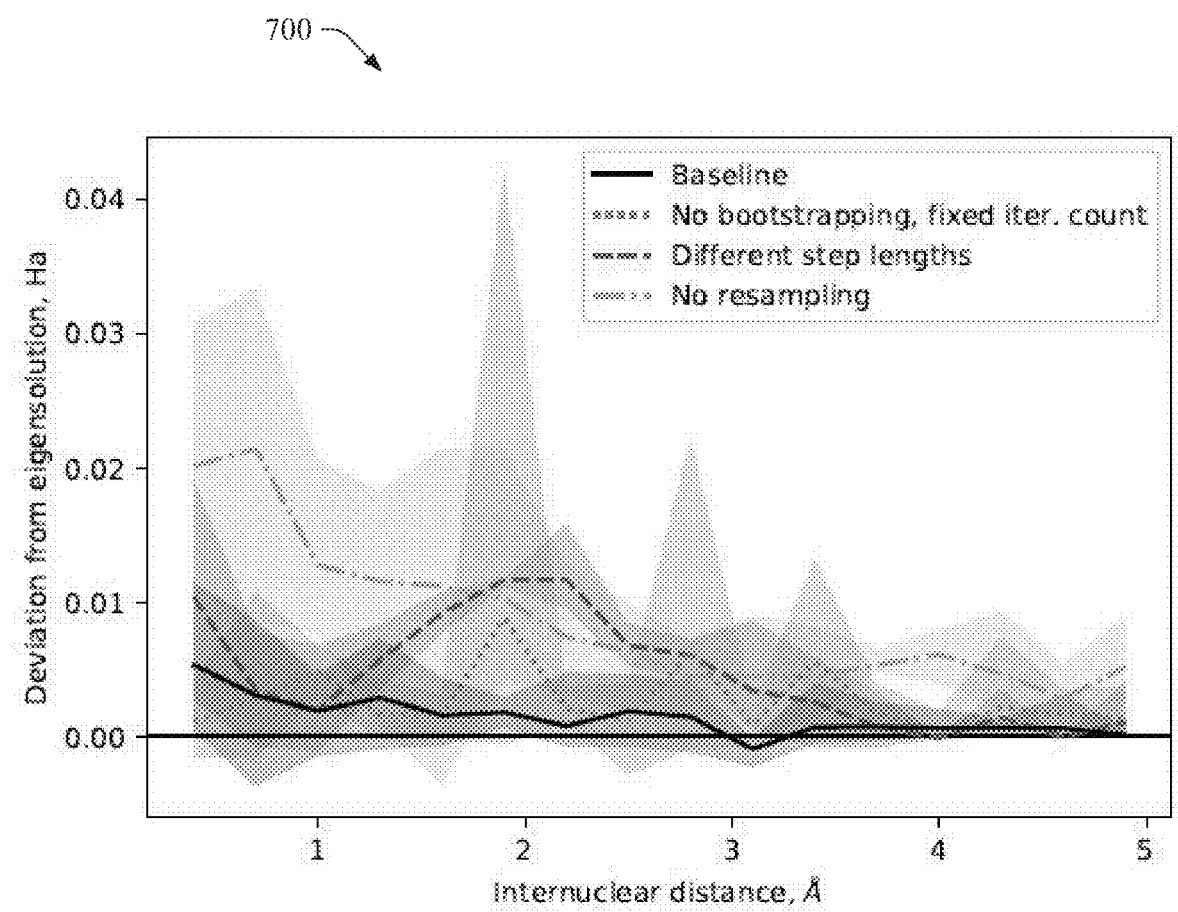
FIG. 7 illustrate diagrams of example, non-limiting graphs that can demonstrate the efficacy of one or more computation processes implemented by an optimization algorithm during execution of a VQE algorithm in accordance with one or more embodiments described herein.

FIG. 7 illustrate diagrams of example, non-limiting graph 700 that can depict the efficacy of the one or more computation processes implemented by the optimizer component 114 in accordance with one or more embodiments described herein. Repetitive description of like elements employed in other embodiments described herein is omitted for sake of brevity. For example, the cyan curve of graph 700 can depict the effects of implementing the bootstrapping computation process, the yellow curve of graph 700 can depict the effects of implementing the resampling computation process, and/ or the magenta curve of graph 700 can depict the effects of implementing the customizable step length scheduling computation process.

Graph 700 plots deviation of VQE solutions from the exact eigensolution at various internuclear distances. The data represents five VQE solutions at each internuclear distance. The lines depicted in graph 700 can be the average, whereas the shaded regions can show the variation (e.g., minimum to maximum) over these solutions. The "baseline" curve can represent classical simulation results of the quantum experiment. The "no bootstrapping, fixed iter. count" cyan curve can show the effect of using a fixed number of iterations (e.g., 30 iterations) rather than adaptive termination, as well as ignoring warm-start information. The "different step length" magenta curve can show the effect of using a step length schedule of 1/k, which tends to get trapped in local minima (e.g., as evident around 2 Å). The "no resampling" yellow curve can show the effect of not repeating the energy estimation and averaging to obtain a more accurate energy estimate.

As depicted in FIG. 7, omitting any one of these computation processes can lead to either a greater error somewhere in the dissociation curve (e.g., compared to the same eigensolution), or greater variation across repeated experiments. For example, the effect of adaptive termination can be to improve computational time (e.g., which can be most apparent when combined with the bootstrapping computation process). In the experiments performed to achieve the depicted data, the highest number of iterations required for any data point is 30. Fixing the number of iterations to 30 and ignoring start information to obtain a no bootstrapping fixed iteration count can results in an execution time that takes up to three times longer than when the adaptive termination computation process is implemented.

Figure 8:
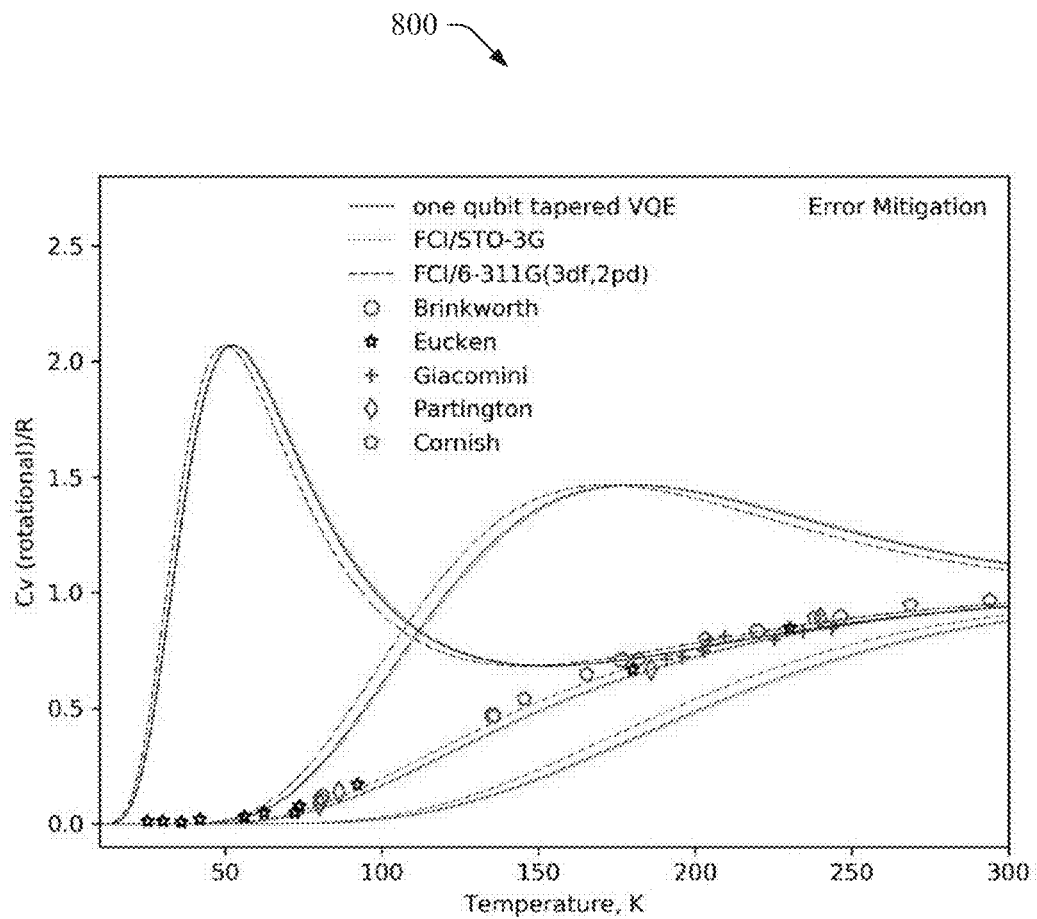
FIG. 8 illustrates a diagram of an example, non-limiting graph that can demonstrate the chemical accuracy of one or more quantum-based computations in determining thermodynamic observables in accordance with one or more embodiments described herein.

FIG. 8 illustrates a diagram of an example, non-limiting graph 800 that can demonstrate the chemical accuracy that can be achieved by the system 100 in accordance with one or more embodiments described herein. Repetitive description of like elements employed in other embodiments described herein is omitted for sake of brevity. FIG. 8 regards the rotational component of the heat capacity $C_v$ of hydrogen. The heat capacity of the molecules of the chemical system was determined by the observables component 602 based on a rotational partition function computed by the partition component 502 in accordance with the various embodiments described herein (e.g., based on rotational modes computed via Equations 21, 23, and/or 24, which was based on a dissociation curve computed by the VQE component 122 and/or optimizer component 114 and/or fitted with a potential energy function by the potential energy component 302). Further, the VQE algorithm was executed on quantum computer 108 comprising five superconducting transmon qubits.

Graph 800 shows the rotational heat capacity of ortho-, para-, equilibrium-, and normal-$H_2$ calculated by VQE/STO-3G, and compared with experimental data for normal-$H_2$, as described herein. The rotational heat capacity can be the heat capacity computed using only the rotational part of the partition function. The VQE/STO-3G calculation substantially agrees with the FCI/STO-3G reference calculation, indicating that the methods used to mitigate noisy quantum computer single-point energies were effective. In addition, the close agreement with experimental data for normal-$H_2$ shows that the VQE/STO-3G procedure provides single-point energies of sufficient accuracy to enable accurate predictions of heat capacity. The FCI/6-3-311G(3df,2pd) single point energies were also used to calculate rotational heat capacity via the Morse potential and partition function method. These results (e.g., also in graph 800) exhibited better agreement with the experimental data (e.g., regarding the conventional experiments of Brinkworth, Eucken, Giacomini, Partington, and/or Cornish) for normal-$H_2$ compared to results using the STO-3G basis set (as would be expected).

Solid lines of graph 800 can represent the constant volume rotational heat capacity calculation derived from: the quantum computer single-point energy calculations, the Morse-potential fit, and the resulting partition function. Black, blue, red, and green represent the equilibrium mixture, para-, ortho-, and normal $H_2$, respectively. Dotted and dot-dashed lines are also derived from the Morse-potential fit, and the resulting partition function, but single point energies are computed by classical computer at the FCI/STO-3G and FCI/6-311G(3df,2pd) levels of theory, respectively. Markers represent experimental data measured on normal $H_2$. The sub-figure shows the fraction of para-$H_2$ as a function of temperature. Solid and dot-dashed lines represent the quantum computer 108 and classical calculations, as described above.

Figure 9:
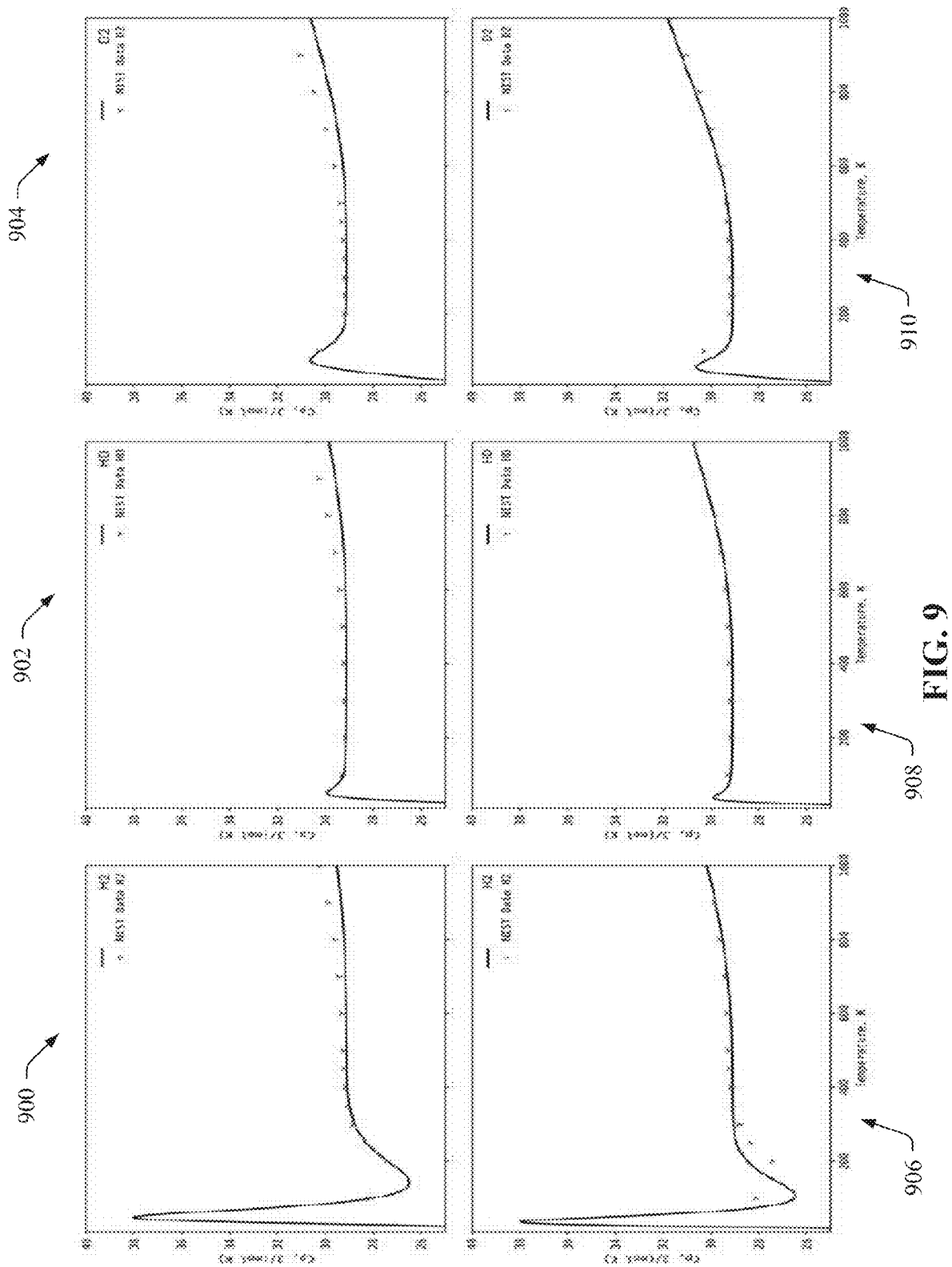
FIG. 9 illustrates a diagram of example, non-limiting graphs that can demonstrate the chemical accuracy of one or more quantum-based computations in determining thermodynamic observables in accordance with one or more embodiments described herein.

FIG. 9 illustrates a diagram of example, non-limiting graphs 900, 902, and 904 that can regard thermodynamic observables computed by the system 100 on a five qubit quantum computer 108, and graphs 906, 908, and 910 that can regard thermodynamic observables computed by the system 100 on a 20 qubit quantum computer 108 in accordance with one or more embodiments described herein. Repetitive description of like elements employed in other embodiments described herein is omitted for sake of brevity. FIG. 9 also regards the chemical system: $H_2+D_2 \rightarrow 2HD$.

As a chemical system increases in size and/or complexity, the number of qubits required to execute the VQE algorithm also increases. However, as the number of qubits in the utilized quantum computers 108 increase, so does the amount of noise inherently incorporated into the resulting data. Consequently, conventional computation methods are inhibited in an attempt to analyze large chemical systems due to the loss of chemical accuracy caused by the additional noise.

As described herein, the computation methods implemented by the system 100, in accordance with the various embodiments, can mitigate the amount of noise inherently added by the quantum hardware. FIG. 9 demonstrates the efficacy of the system's 100 noise mitigation by providing a side-by-side comparison of equivalent computations performed on quantum computers comprising 5 and 20 superconducting qubits. For both calculations the size of the chemical system is the same and only a single qubit was used on both the 5 and 20 qubit quantum computers 108. As shown in FIG. 9 the system 100 can compute thermodynamic observables on the 20 qubit quantum computer 108 with nearly the same chemical accuracy as when computed on the 5 qubit quantum computer 108; thereby, demonstrating that the various embodiments described herein can be scaled based on the size and/or complexity of the chemical system while maintaining a desired level of chemical accuracy.

Graphs 900, 902, 904, 906, 908, and/or 910 further depict data points regard the given chemical system from the National Institute of Standards and Technology ("NIST") to illustrate the chemical accuracy of the computed thermodynamic observable. For example, graphs 900 and 906 show a side-by-side comparison of the heat capacity of the $H_2$ molecule of the given chemical system computed on the 5 qubit quantum computer 108 (e.g., graph 900) and the 20 qubit quantum computer 108 (e.g., graph 906). Graphs 902 and 908 show a side-by-side comparison of the heat capacity of the HD molecule of the given chemical system computed on the 5 qubit quantum computer 108 (e.g., graph 902) and the 20 qubit quantum computer 108 (e.g., graph 908). Also, graphs 904 and 910 show a side-by-side comparison of the heat capacity of the $D_2$ molecule of the given chemical system computed on the 5 qubit quantum computer 108 (e.g., graph 904) and the 20 qubit quantum computer 108 (e.g., graph 910).

Figure 10:
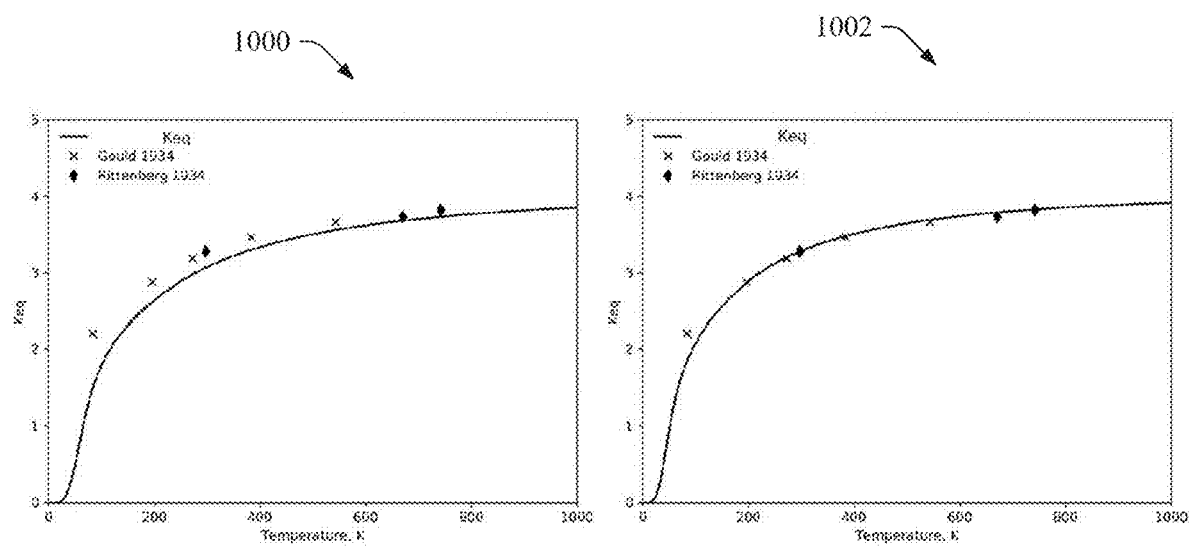
FIG. 10 illustrates a diagram of example, non-limiting graphs that can demonstrate the chemical accuracy of one or more quantum-based computations in determining an equilibrium constant in accordance with one or more embodiments described herein.

FIG. 10 illustrates a diagram of example, non-limiting graphs 1000 and 1002, which can demonstrate the efficacy of the computational methods implemented by the system 100 in accordance with one or more embodiments described herein. Repetitive description of like elements employed in other embodiments described herein is omitted for sake of brevity. FIG. 10 also regards the chemical system: $H_2+D_2 \rightarrow 2HD$.

Graph 1000 depicts the chemical equilibrium for the given chemical system as computed by the system 100 using a quantum computer 108 comprising 5 superconducting qubits. Graph 1002 depicts the chemical equilibrium for the given chemical system as computed by the system 100 using a quantum computer 108 comprising 20 superconducting qubits. Additionally, data points regarding the conventional experimentation schemes (e.g., Gould 1934 and/or Rittenberg 1934) are also depicted on graphs 1000 and 1002 to demonstrate the chemical accuracy of the computed chemical equilibrium. FIG. 10 further demonstrates that the various embodiments of the system 100 described herein can compute thermodynamic observables with high chemical accuracy and can be scaled to analyzed large and/or complex chemical systems.

Figure 11:
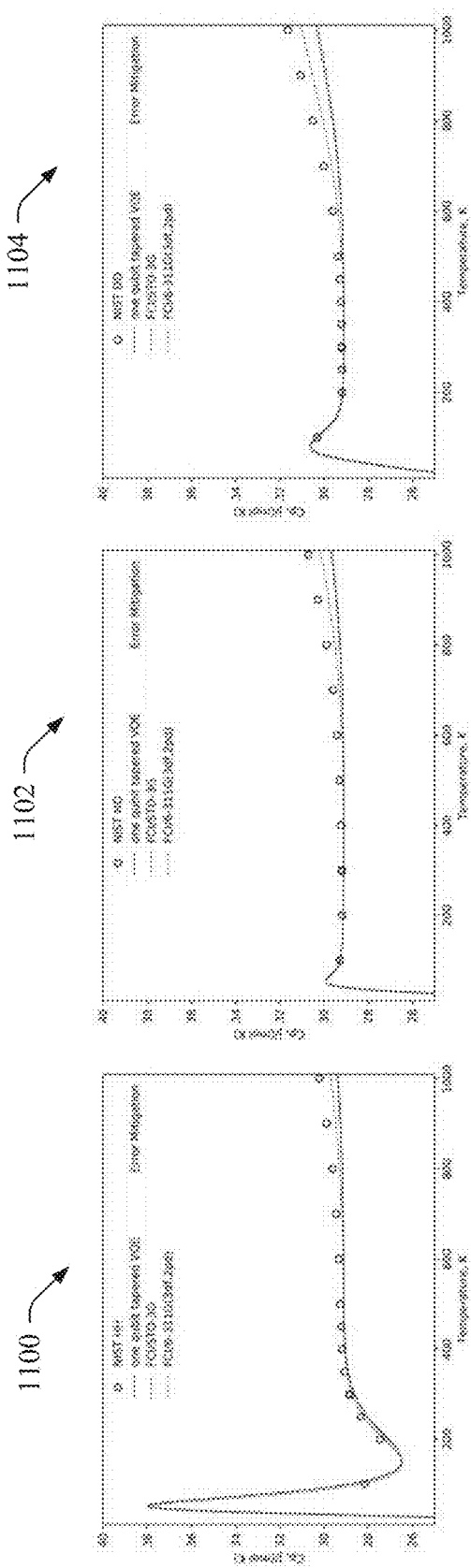
FIG. 11 illustrates a diagram of an example, non-limiting graph that can demonstrate the chemical accuracy of one or more quantum-based computations in determining thermodynamic observables in accordance with one or more embodiments described herein.
Figure 12:
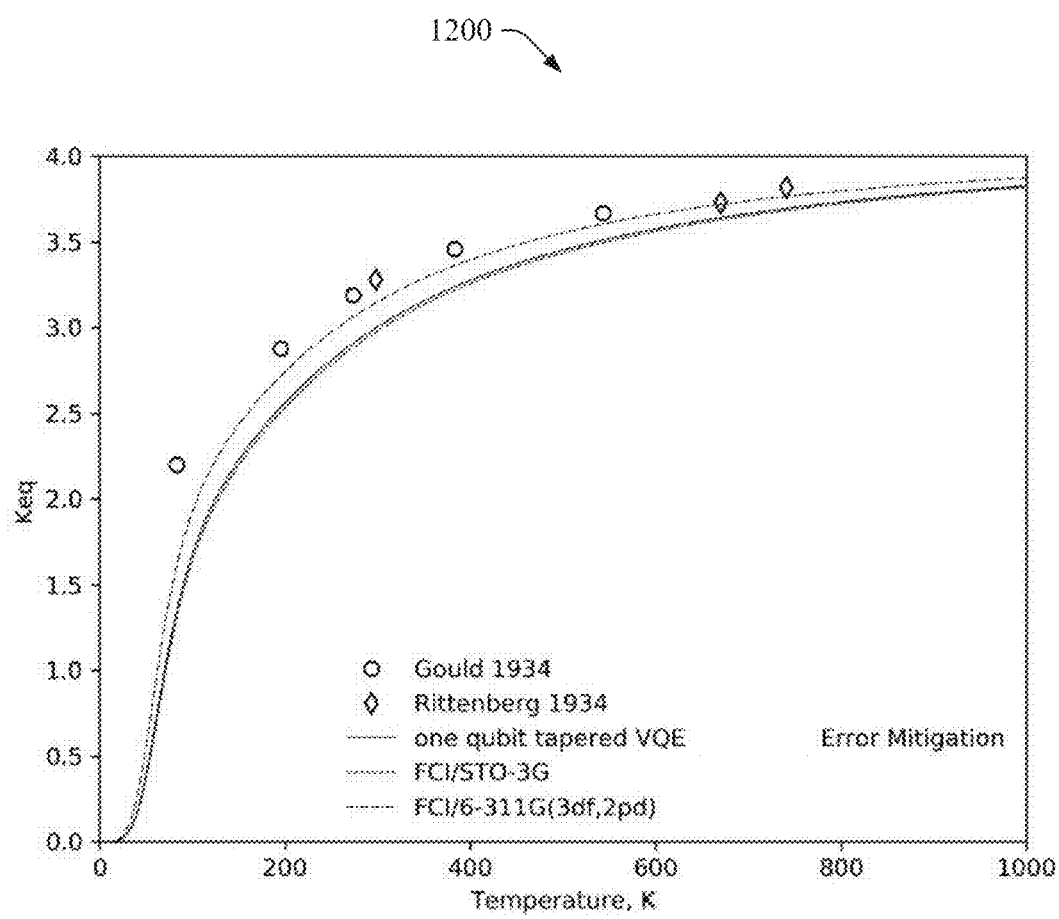
FIG. 12 illustrates a diagram of example, non-limiting graphs that can demonstrate the chemical accuracy of one or more quantum-based computations in determining thermodynamic observables in accordance with one or more embodiments described herein.

FIGS. 11 and 12 illustrate diagrams of example, non-limiting graphs that can further demonstrate the efficacy of the computational methods implemented by the system 100 in accordance with one or more embodiments described herein. Repetitive description of like elements employed in other embodiments described herein is omitted for sake of brevity. FIGS. 11-12 also regard the chemical system: $H_2+D_2 \rightarrow 2HD$, and can facilitate a comparison of a quantum hardware simulation of the computational methods implemented by the system 100 and FCI of the computational methods implemented by the system 100.

Graphs 1102, 1104, and/or 1106 can shows the constant pressure heat capacity as a function of temperature for $H_2$, $D_2$, and HD, also calculated by using the methodology described herein in accordance with one or more embodiments. Here, the nuclear spin is taken into account regarding the rotational coupling for $H_2$, $D_2$. This is not necessary for HD since the nuclei are not identical. Experimental data is from NIST. As with the rotational heat capacity (e.g., shown in graph 800) the calculations on the quantum computer 108 agree substantially with the FCI/STO-3G results, although and the FCI/6-3-311G(3df,2pd) results are closer to the experimental data as temperature increases.

Graph 1200 can depict the computed chemical equilibrium in the same manner as graph 1000; wherein the solid lines can represent quantum hardware simulations (e.g., with error mitigation in the VQE algorithm) of the computational methods implemented by the system 100, and the dashed lines can represent FCIs of computational methods implemented by the system 100 (e.g., two sets of dashed lines delineating two FCI embodiments).

Figure 13:
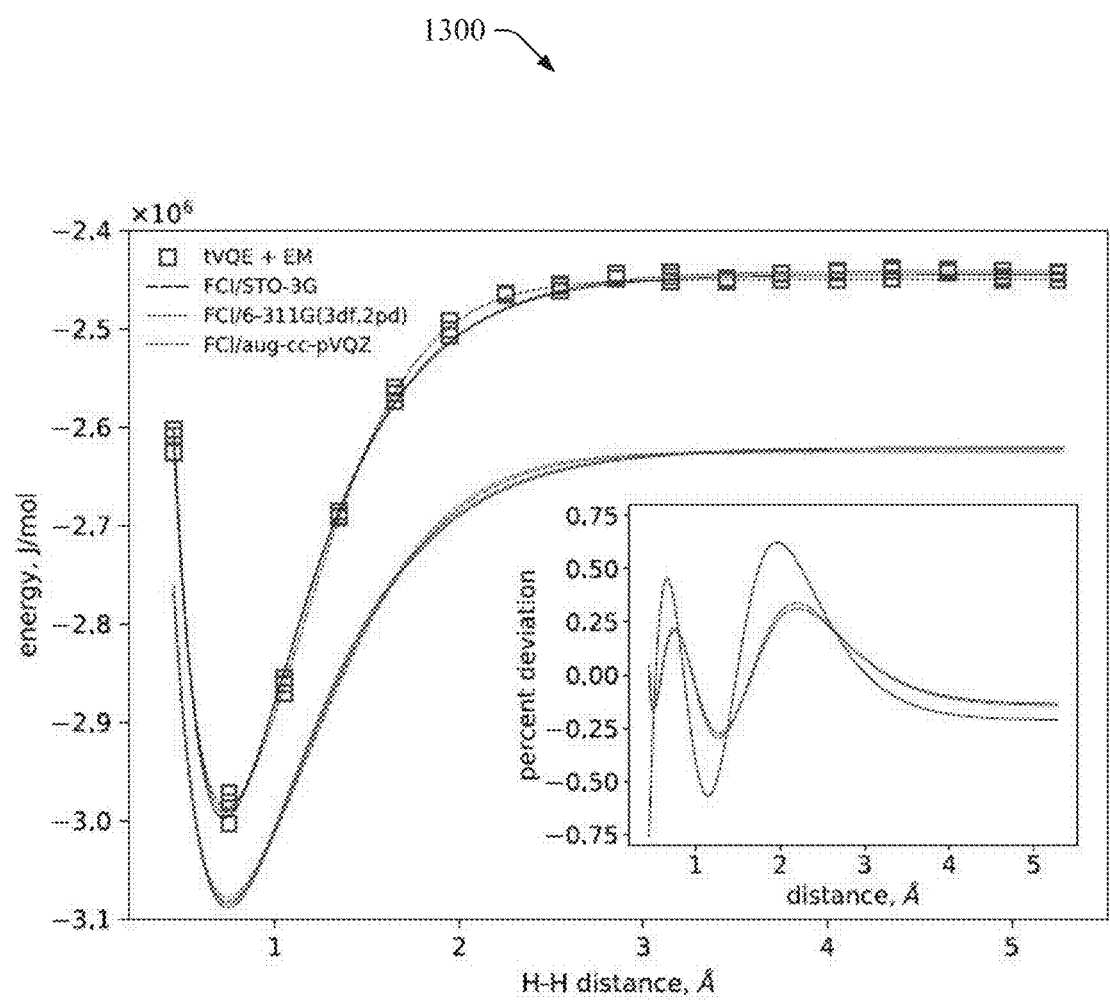
FIG. 13 illustrates a diagram of an example, non-limiting graph that can demonstrate the chemical accuracy of one or more quantum-based computations in determining thermodynamic observables in accordance with one or more embodiments described herein.

FIG. 13 illustrates a diagram of an example, non-limiting graph 1300 that can regard an exemplary fitting of a Morse potential function to a dissociation curve in accordance with one or more embodiments described herein. Repetitive description of like elements employed in other embodiments described herein is omitted for sake of brevity.

In the main figure of graph 1300, solid lines can represent Morse potential fits of the calculated single-point energies. Dashed lines can represent calculations on a classical computer, every is 0.01 Å from 0.45 to 5.3 Å, at the level of theory listed in the legend. Green squares are the calculations using the quantum computer 108. The sub-figure of graph 1300 shows the percent deviation between the Morse potential fit and the FCI/STO-3G, FCI/6-311G(3df,2pd), and FCI/aug-cc-pVQZ calculations, in black, red, and blue, respectively, as a function of distance. the deviation of the Morse potential fit of single-point energies from the single-point calculations themselves. These results demonstrate that as the size of the basis set increases, there can be a limit beyond which the Morse potential fit does not improve (e.g., the functional form of the Morse potential does not describe the real potential energy surface with accuracy).

When compared to experimental data, the computation methods implemented by the system 100 and/or described herein can be capable of achieving chemical accuracy, ±1 kilocalorie per mole (kcal/mol). Tables 1, 2, and/or 3 show the constant pressure heat capacity, entropy, and enthalpy and free energy of reaction, calculated at standard conditions (e.g., 298.15 Kelvin (K), 1 bar) using single-point energies from the quantum computer 108, fitting the Morse potential to the dissociation curve, and/or determining the partition function in accordance with the various embodiments described herein. Compared to experimental results from NIST, the data of Tables 1, 2, and/or 3 can show that techniques described herein with regards to one or more embodiments can enable chemically accurate calculations using noisy intermediate-scale quantum devices.

Table 1 regards the constant pressure heat capacity at standard conditions (298.15 K, 1 bar) derived from the quantum computer single-point energy calculations, the Morse potential fit, and the resulting partition function (denoted $Cp^\Phi$(VQE)) and NIST experimental data. The last column shows the error of the quantum calculation compared to experiment.

TABLE 1

| | $Cp^\Phi$ (VQE) cal mol$^{-1}$ K$^{-1}$ | $Cp^\Phi$ (NIST) cal mol$^{-1}$ K$^{-1}$ | Error cal mol$^{-1}$ K$^{-1}$ |
|---|---|---|---|
| $H_2$ | 6.83 | 6.89 | −0.06 |
| HD | 6.96 | 6.98 | −0.02 |
| $D_2$ | 6.96 | 6.98 | −0.02 |

Table 2 regards the constant pressure heat capacity at standard conditions (298.15 K, 1 bar) derived from the quantum computer single-point energy calculations, the Morse potential fit, and the resulting partition function (denoted $S^\Phi$(VQE)) and NIST experimental data. The last column shows the error of the quantum calculation compared to experiment.

TABLE 2

| | $S^\Phi$ (VQE) cal mol$^{-1}$ K$^{-1}$ | $S^\Phi$ (NIST) cal mol$^{-1}$ K$^{-1}$ | Error cal mol$^{-1}$ K$^{-1}$ |
|---|---|---|---|
| $H_2$ | 29.08 | 31.23 | −2.16 |
| HD | 32.29 | 34.65 | −2.35 |
| $D_2$ | 32.65 | 34.37 | −1.72 |

Table 3 regards the constant pressure heat capacity at standard conditions (298.15 K, 1 bar) derived from the quantum computer single-point energy calculations, the Morse potential fit, and the resulting partition function (denoted VQE) and NIST experimental data. The last column shows the error of the quantum calculation compared to experiment.

TABLE 3

| $H_2 + D_2 \rightleftharpoons 2HD$ | VQE kcal mol$^{-1}$ | NIST kcal mol$^{-1}$ | Error kcal mol$^{-1}$ |
|---|---|---|---|
| $\Delta H_{rxn}^{\ominus}$ | 0.20 | 0.15 | 0.05 |
| $\Delta G_{rxn}^{\ominus}$ | −0.65 | −0.70 | 0.05 |

Figure 14:
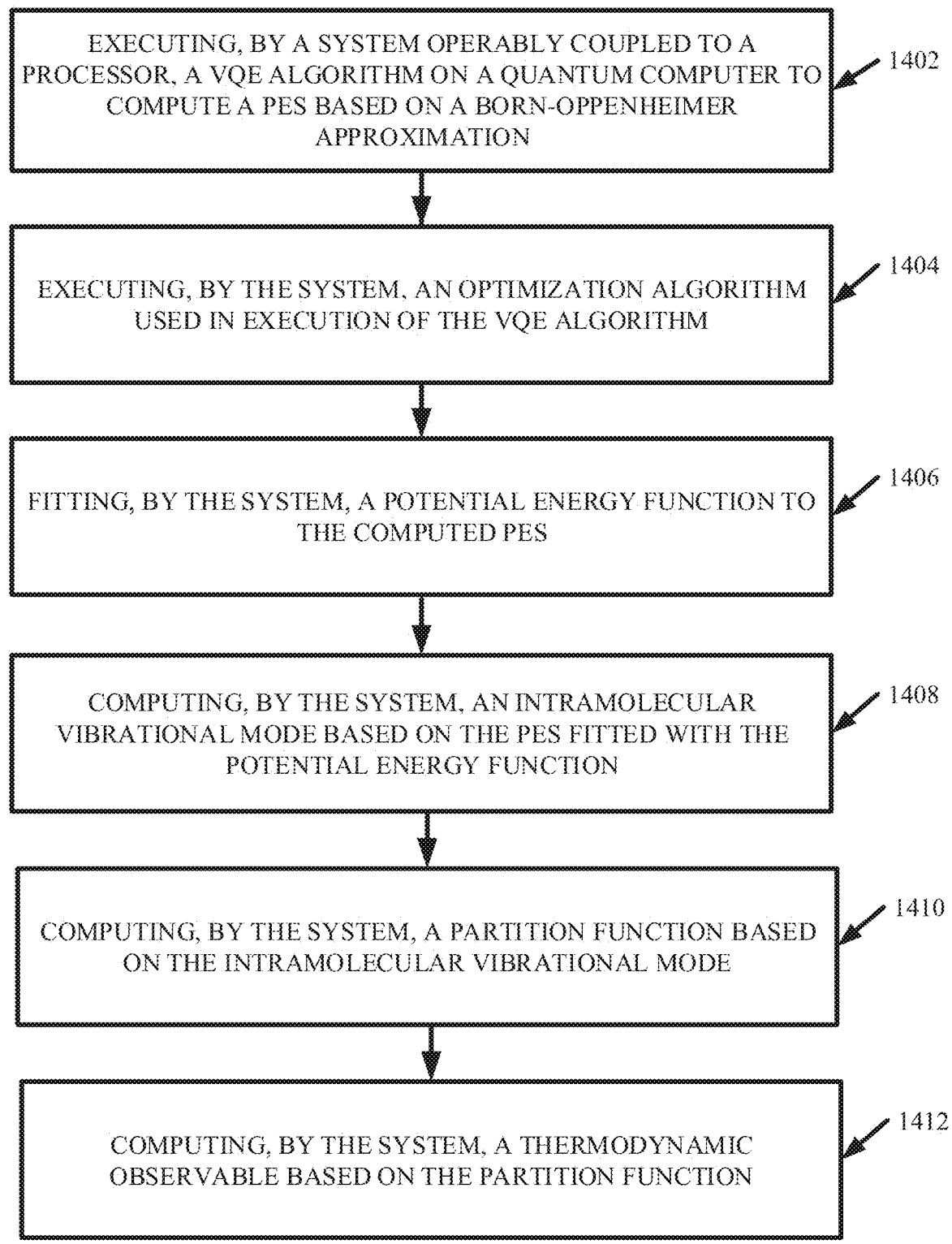
FIG. 14 illustrates a flow diagram of an example, non-limiting computer-implemented method that can facilitate determining one or more thermodynamic observables via quantum-based computations in accordance with one or more embodiments described herein.

FIG. 14 illustrates a flow diagram of an example, non-limiting computer-implemented method 1400 that can facilitate determining one or more thermodynamic observables of chemical system based on one or more quantum computations in accordance with one or more embodiments described herein. Repetitive description of like elements employed in other embodiments described herein is omitted for sake of brevity.

At 1402, the computer-implemented method 1400 can comprise executing (e.g., via VQE component 122), by a system 100 operably coupled to a processor 120, one or more VQE algorithms on one or more quantum computers 108 to compute a potential energy surface ("PES") of one or more molecules based on one or more Born-Oppenheimer approximations. At 1404, the computer-implemented method 1400 can comprise executing (e.g., via optimizer component 114), by the system 100, one or more optimization algorithms used in execution of the one or more VQE algorithms of 1402. For example, the optimization algorithm can comprise one or more computation processes, such as: adaptive termination, resampling, bootstrapping, a combination thereof, and/or the like.

At 1406, the computer-implemented method 1400 can comprise fitting (e.g., via potential energy component 302), by the system 100, one or more potential energy functions to the computed PBS. For example, the one or more potential energy functions can be Morse potential energy functions. At 1408, the computer-implemented method 1400 can comprise computing (e.g., via the vibrational mode component 402), by the system 100, one or more intramolecular vibrational modes based on the PES fitted with the potential energy function. At 1410, the computer-implemented method 1400 can comprise computing (e.g., via the partition component 502), by the system 100, one or more partition functions based on the one or more intramolecular vibrational modes. For example, the one or more partition functions computed as 1410 can comprise vibrational and/or rotational partition functions. At 1412, the computer-implemented method 1400 can comprise computing (e.g., via observables component 602), by the system 100, one or more thermodynamic observables based on the partition function. For example, the one or more thermodynamic observables can include, but are not limited to: entropy, internal energy, enthalpy, Gibbs free energy, heat capacity, a reaction equilibrium constant, and/or a combination thereof.

Figure 15:
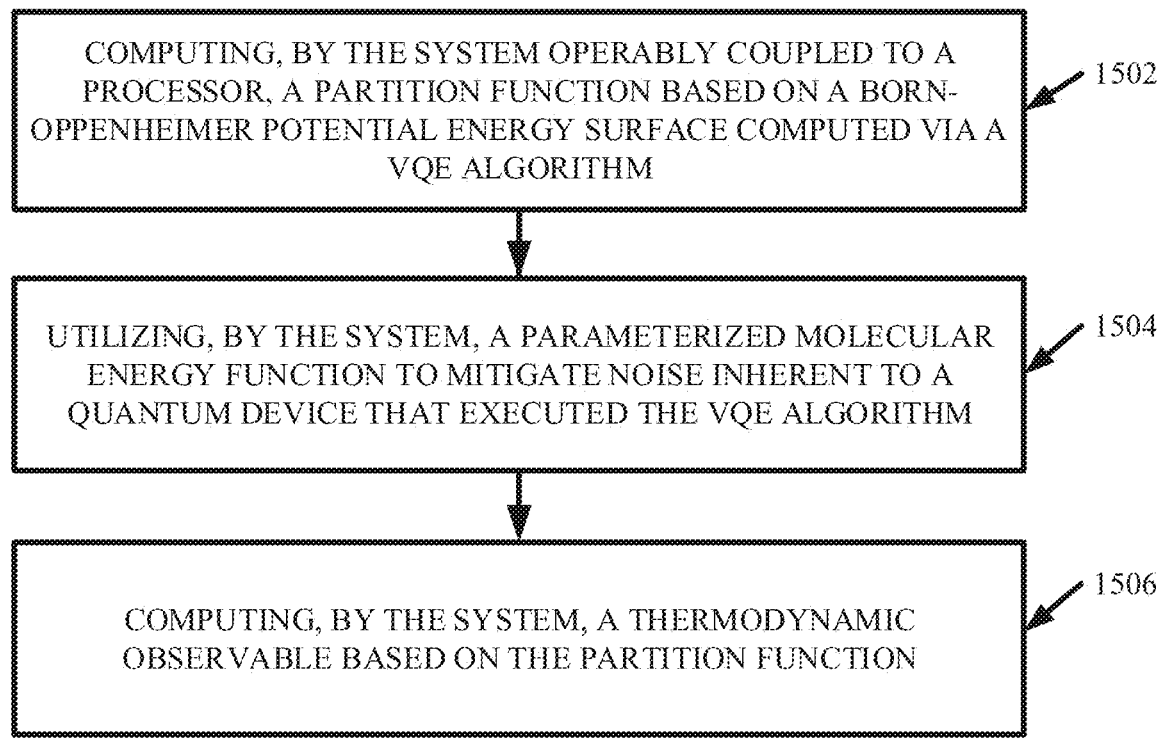
FIG. 15 illustrates a flow diagram of an example, non-limiting computer-implemented method that can facilitate determining one or more thermodynamic observables via quantum-based computations in accordance with one or more embodiments described herein.

FIG. 15 illustrates a flow diagram of an example, non-limiting computer-implemented method 1500 that can facilitate determining one or more thermodynamic observables of chemical system based on one or more quantum computations in accordance with one or more embodiments described herein. Repetitive description of like elements employed in other embodiments described herein is omitted for sake of brevity.

At 1502, the computer-implemented method 1500 can comprise computing (e.g., via computations component 110), by a system 100 operably coupled to a processor 120, one or more partition functions based on a BOPES computed via one or more VQE algorithms (e.g., by VQE component 122 and/or optimizer component 114). At 1504, the computer-implemented method 1500 can comprise utilizing (e.g., via potential energy component 302), by the system 100, a parameterized molecular energy function to mitigate noise inherent to one or more quantum devices that executed the VQE algorithm. For example, one or more molecular potential energy functions can be fitted to a dissociation curve generated by the VQE algorithm to derive the parameterized molecular energy function. At 1506, the computer-implemented method 1500 can comprise computing (e.g., via observables component 602), by the system 100, one or more thermodynamic observables based on the one or more partition functions. For example, the one or more thermodynamic observables can include, but are not limited to: entropy, internal energy, enthalpy, Gibbs free energy, heat capacity, a reaction equilibrium constant, and/or a combination thereof.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 16:
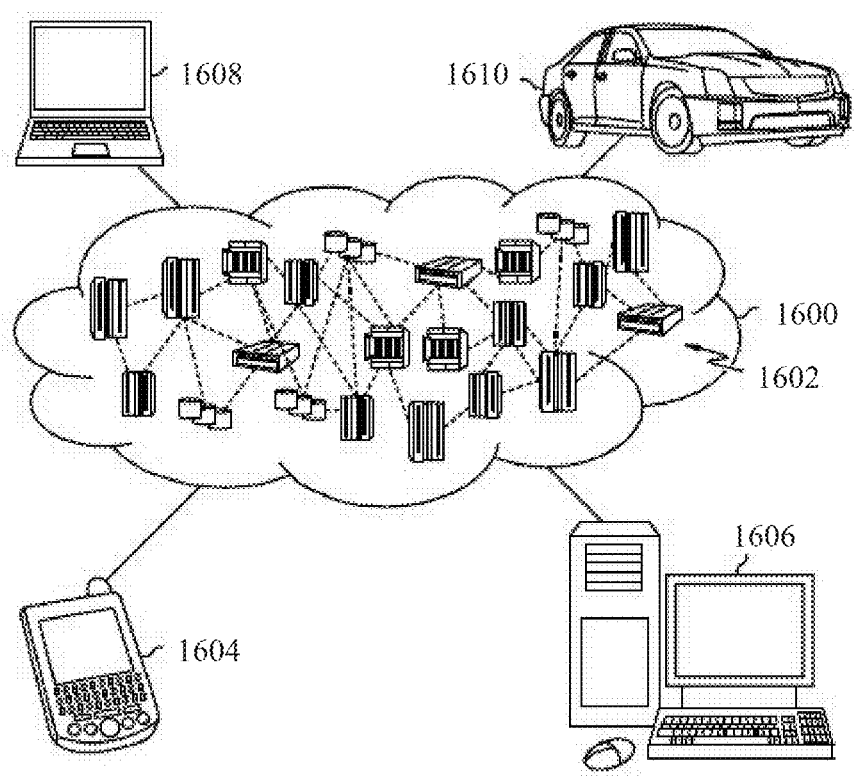
FIG. 16 depicts a cloud computing environment in accordance with one or more embodiments described herein.

Referring now to FIG. 16, illustrative cloud computing environment 1600 is depicted. As shown, cloud computing environment 1600 includes one or more cloud computing nodes 1602 with which local computing devices used by cloud consumers, such as, for example, personal digital assistant (PDA) or cellular telephone 1604, desktop computer 1606, laptop computer 1608, and/or automobile computer system 1610 may communicate. Nodes 1602 may communicate with one another. They may be grouped (not shown) physically or virtually, in one or more networks, such as Private, Community, Public, or Hybrid clouds as described hereinabove, or a combination thereof. This allows cloud computing environment 1600 to offer infrastructure, platforms and/or software as services for which a cloud consumer does not need to maintain resources on a local computing device. It is understood that the types of computing devices 1604-1610 shown in FIG. 16 are intended to be illustrative only and that computing nodes 1602 and cloud computing environment 1600 can communicate with any type of computerized device over any type of network and/or network addressable connection (e.g., using a web browser).

Figure 17:
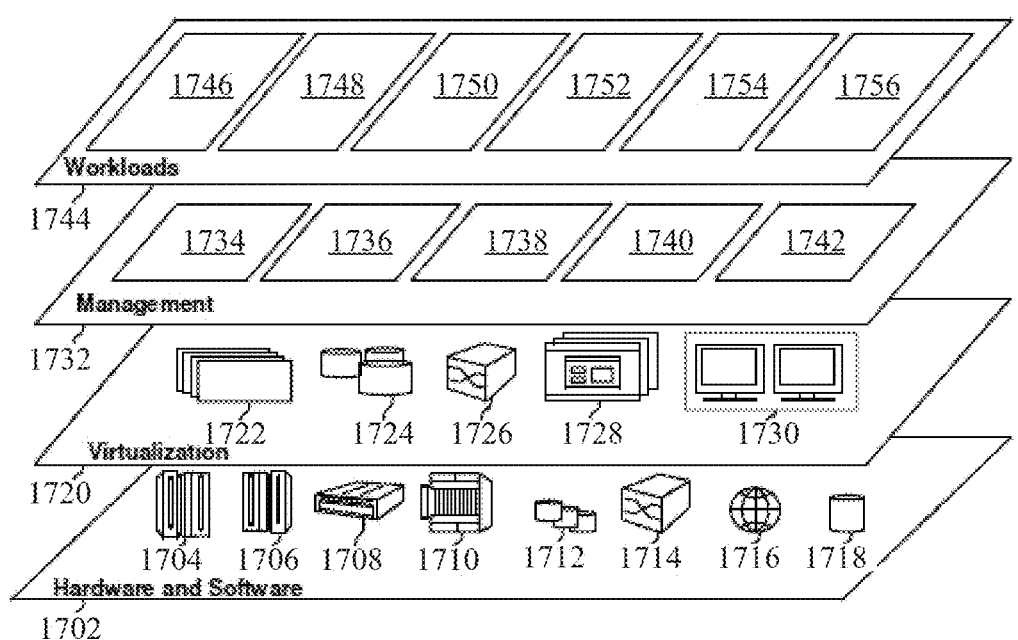
FIG. 17 depicts abstraction model layers in accordance with one or more embodiments described herein

Referring now to FIG. 17, a set of functional abstraction layers provided by cloud computing environment 1600 (FIG. 16) is shown. Repetitive description of like elements employed in other embodiments described herein is omitted for sake of brevity. It should be understood in advance that the components, layers, and functions shown in FIG. 17 are intended to be illustrative only and embodiments of the invention are not limited thereto. As depicted, the following layers and corresponding functions are provided.

Hardware and software layer 1702 includes hardware and software components. Examples of hardware components include: mainframes 1704; RISC (Reduced Instruction Set Computer) architecture based servers 1706; servers 1708; blade servers 1710; storage devices 1712; and networks and networking components 1714. In some embodiments, software components include network application server software 1716 and database software 1718.

Virtualization layer 1720 provides an abstraction layer from which the following examples of virtual entities may be provided: virtual servers 1722; virtual storage 1724; virtual networks 1726, including virtual private networks; virtual applications and operating systems 1728; and virtual clients 1730.

In one example, management layer 1732 may provide the functions described below. Resource provisioning 1734 provides dynamic procurement of computing resources and other resources that are utilized to perform tasks within the cloud computing environment. Metering and Pricing 1736 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1738 provides access to the cloud computing environment for consumers and system administrators. Service level management 1740 provides cloud computing resource allocation and management such that required service levels are met. Service Level Agreement (SLA) planning and fulfillment 1742 provide pre-arrangement for, and procurement of, cloud computing resources for which a future requirement is anticipated in accordance with an SLA.

Workloads layer 1744 provides examples of functionality for which the cloud computing environment may be utilized. Examples of workloads and functions which may be provided from this layer include: mapping and navigation 1746; software development and lifecycle management 1748; virtual classroom education delivery 1750; data analytics processing 1752; transaction processing 1754; and VQE algorithm execution 1756. Various embodiments of the present invention can utilize the cloud computing environment described with reference to FIGS. 16 and 17 to facilitate communications and/or computations between classical computing hardware (e.g., one or more components of server 102) and quantum computing hardware (e.g., quantum computers 108) during the execution of one or more VQE algorithms.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware based systems that perform the specified functions or acts or carry out combinations of special purpose hardware and computer instructions.

Figure 18:
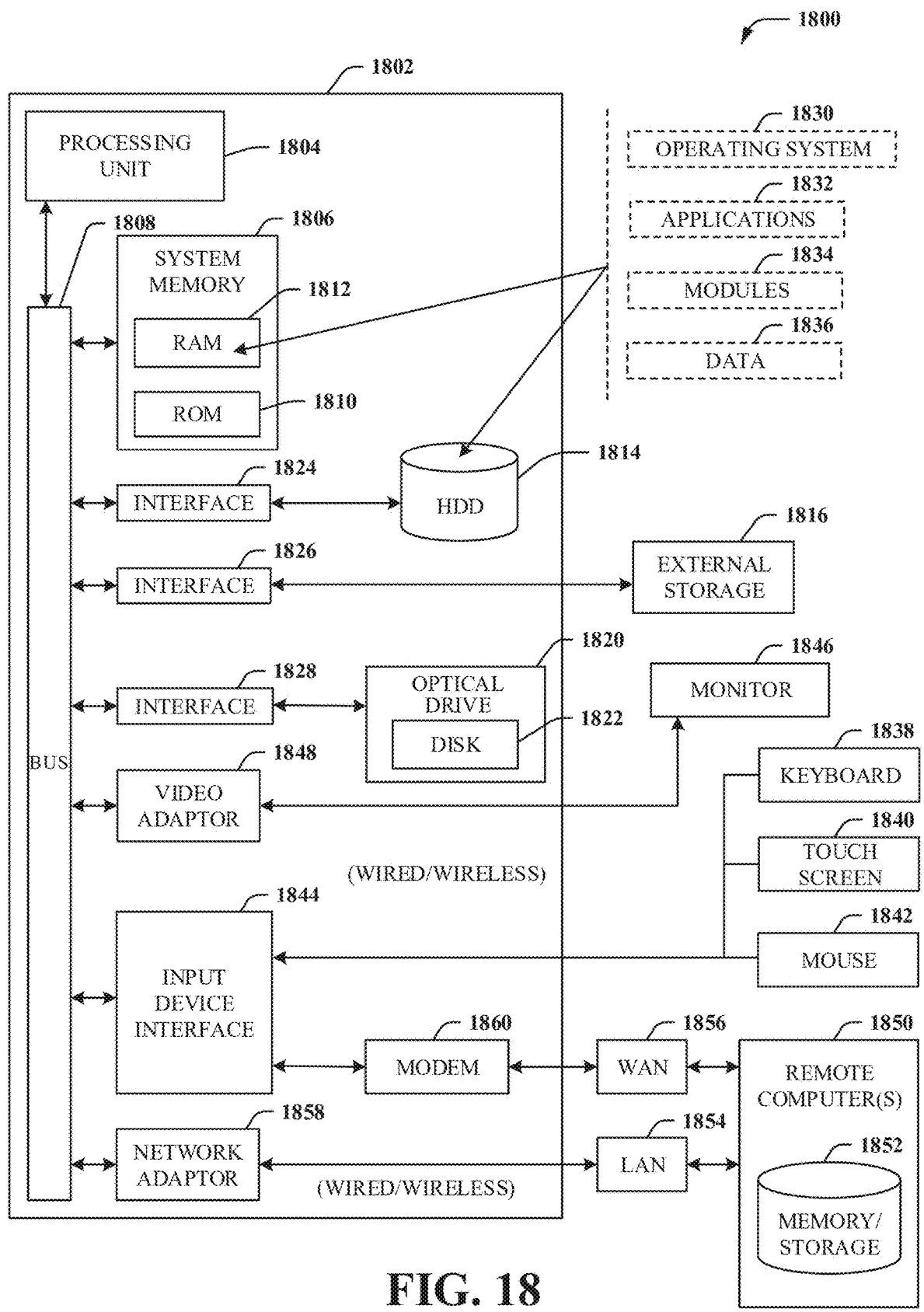
FIG. 18 illustrates a block diagram of an example, non-limiting operating environment in which one or more embodiments described herein can be facilitated.

In order to provide additional context for various embodiments described herein, FIG. 18 and the following discussion are intended to provide a general description of a suitable computing environment 1800 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things ("IoT") devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices. For example, in one or more embodiments, computer executable components can be executed from memory that can include or be comprised of one or more distributed memory units. As used herein, the term "memory" and "memory unit" are interchangeable. Further, one or more embodiments described herein can execute code of the computer executable components in a distributed manner, e.g., multiple processors combining or working cooperatively to execute code from one or more distributed memory units. As used herein, the term "memory" can encompass a single memory or memory unit at one location or multiple memories or memory units at one or more locations.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory ("RAM"), read only memory ("ROM"), electrically erasable programmable read only memory ("EEPROM"), flash memory or other memory technology, compact disk read only memory ("CD-ROM"), digital versatile disk ("DVD"), Blu-ray disc ("BD") or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 18, the example environment 1800 for implementing various embodiments of the aspects described herein includes a computer 1802, the computer 1802 including a processing unit 1804, a system memory 1806 and a system bus 1808. The system bus 1808 couples system components including, but not limited to, the system memory 1806 to the processing unit 1804. The processing unit 1804 can be any of various commercially available processors. Dual microprocessors and other multi-processor architectures can also be employed as the processing unit 1804.

The system bus 1808 can be any of several types of bus structure that can further interconnect to a memory bus (with or without a memory controller), a peripheral bus, and a local bus using any of a variety of commercially available bus architectures. The system memory 1806 includes ROM 1810 and RAM 1812. A basic input/output system ("BIOS") can be stored in a non-volatile memory such as ROM, erasable programmable read only memory ("EPROM"), EEPROM, which BIOS contains the basic routines that help to transfer information between elements within the computer 1802, such as during startup. The RAM 1812 can also include a high-speed RAM such as static RAM for caching data.

The computer 1802 further includes an internal hard disk drive ("HDD") 1814 (e.g., EIDE, SATA), one or more external storage devices 1816 (e.g., a magnetic floppy disk drive ("FDD") 1816, a memory stick or flash drive reader, a memory card reader, etc.) and an optical disk drive 1820 (e.g., which can read or write from a CD-ROM disc, a DVD, a BD, etc.). While the internal HDD 1814 is illustrated as located within the computer 1802, the internal HDD 1814 can also be configured for external use in a suitable chassis (not shown). Additionally, while not shown in environment 1800, a solid state drive ("SSD") could be used in addition to, or in place of, an HDD 1814. The HDD 1814, external storage device(s) 1816 and optical disk drive 1820 can be connected to the system bus 1808 by an HDD interface 1824, an external storage interface 1826 and an optical drive interface 1828, respectively. The interface 1824 for external drive implementations can include at least one or both of Universal Serial Bus ("USB") and Institute of Electrical and Electronics Engineers ("IEEE") 1394 interface technologies. Other external drive connection technologies are within contemplation of the embodiments described herein.

The drives and their associated computer-readable storage media provide nonvolatile storage of data, data structures, computer-executable instructions, and so forth. For the computer 1802, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1812, including an operating system 1830, one or more application programs 1832, other program modules 1834 and program data 1836. All or portions of the operating system, applications, modules, and/or data can also be cached in the RAM 1812. The systems and methods described herein can be implemented utilizing various commercially available operating systems or combinations of operating systems.

Computer 1802 can optionally comprise emulation technologies. For example, a hypervisor (not shown) or other intermediary can emulate a hardware environment for operating system 1830, and the emulated hardware can optionally be different from the hardware illustrated in FIG. 18. In such an embodiment, operating system 1830 can comprise one virtual machine ("VM") of multiple VMs hosted at computer 1802. Furthermore, operating system 1830 can provide runtime environments, such as the Java runtime environment or the .NET framework, for applications 1832. Runtime environments are consistent execution environments that allow applications 1832 to run on any operating system that includes the runtime environment. Similarly, operating system 1830 can support containers, and applications 1832 can be in the form of containers, which are lightweight, standalone, executable packages of software that include, e.g., code, runtime, system tools, system libraries and settings for an application.

Further, computer 1802 can be enable with a security module, such as a trusted processing module ("TPM"). For instance with a TPM, boot components hash next in time boot components, and wait for a match of results to secured values, before loading a next boot component. This process can take place at any layer in the code execution stack of computer 1802, e.g., applied at the application execution level or at the operating system ("OS") kernel level, thereby enabling security at any level of code execution.

A user can enter commands and information into the computer 1802 through one or more wired/wireless input devices, e.g., a keyboard 1838, a touch screen 1840, and a pointing device, such as a mouse 1842. Other input devices (not shown) can include a microphone, an infrared ("IR") remote control, a radio frequency ("RF") remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1804 through an input device interface 1844 that can be coupled to the system bus 1808, but can be connected by other interfaces, such as a parallel port, an IEEE 1394 serial port, a game port, a USB port, an IR interface, a BLUETOOTH® interface, etc.

A monitor 1846 or other type of display device can be also connected to the system bus 1808 via an interface, such as a video adapter 1848. In addition to the monitor 1846, a computer typically includes other peripheral output devices (not shown), such as speakers, printers, etc.

The computer 1802 can operate in a networked environment using logical connections via wired and/or wireless communications to one or more remote computers, such as a remote computer(s) 1850. The remote computer(s) 1850 can be a workstation, a server computer, a router, a personal computer, portable computer, microprocessor-based entertainment appliance, a peer device or other common network node, and typically includes many or all of the elements described relative to the computer 1802, although, for purposes of brevity, only a memory/storage device 1852 is illustrated. The logical connections depicted include wired/wireless connectivity to a local area network ("LAN") 1854 and/or larger networks, e.g., a wide area network ("WAN") 1856. Such LAN and WAN networking environments are commonplace in offices and companies, and facilitate enterprise-wide computer networks, such as intranets, all of which can connect to a global communications network, e.g., the Internet.

When used in a LAN networking environment, the computer 1802 can be connected to the local network 1854 through a wired and/or wireless communication network interface or adapter 1858. The adapter 1858 can facilitate wired or wireless communication to the LAN 1854, which can also include a wireless access point ("AP") disposed thereon for communicating with the adapter 1858 in a wireless mode.

When used in a WAN networking environment, the computer 1802 can include a modem 1860 or can be connected to a communications server on the WAN 1856 via other means for establishing communications over the WAN 1856, such as by way of the Internet. The modem 1860, which can be internal or external and a wired or wireless device, can be connected to the system bus 1808 via the input device interface 1844. In a networked environment, program modules depicted relative to the computer 1802 or portions thereof, can be stored in the remote memory/storage device 1852. It will be appreciated that the network connections shown are example and other means of establishing a communications link between the computers can be used.

When used in either a LAN or WAN networking environment, the computer 1802 can access cloud storage systems or other network-based storage systems in addition to, or in place of, external storage devices 1816 as described above. Generally, a connection between the computer 1802 and a cloud storage system can be established over a LAN 1854 or WAN 1856 e.g., by the adapter 1858 or modem 1860, respectively. Upon connecting the computer 1802 to an associated cloud storage system, the external storage interface 1826 can, with the aid of the adapter 1858 and/or modem 1860, manage storage provided by the cloud storage system as it would other types of external storage. For instance, the external storage interface 1826 can be configured to provide access to cloud storage sources as if those sources were physically connected to the computer 1802.

The computer 1802 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity ("Wi-Fi") and BLUETOOTH® wireless technologies. Thus, the communication can be a predefined structure as with a conventional network or simply an ad hoc communication between at least two devices.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer executable components; and
a processor, operably coupled to the memory, and that executes the computer executable components stored in the memory, wherein the computer executable components comprise:
a variational quantum eigensolver (VQE) component that executes a variational quantum eigensolver algorithm on a quantum computer to compute a potential energy surface of a molecule; and
an optimizer component that executes an optimization algorithm used in execution of the variational quantum eigensolver algorithm;
a potential energy component that fits a potential energy function to the potential energy surface of the molecule, wherein fitting the potential energy function comprises employing a potential energy loss function for a parameterized potential energy surface and using a plurality of VQE calculations across a range of bond lengths of the molecule, thereby fitting a set of parameters of the VQE calculations;
a vibrational mode component that computes an intramolecular vibrational mode of the molecule based on the potential energy surface fitted with the potential energy function; and
a partition component that computes a partition function based on the intramolecular vibrational mode.

2. The system of claim 1, wherein the variational quantum eigensolver component executes the variational quantum eigensolver algorithm based on a Born-Oppenheimer approximation.

3. The system of claim 1, wherein the optimization algorithm further implements an adaptive termination process.

4. The system of claim 1, wherein the potential energy function comprises a Morse potential function.

5. The system of claim 1, further comprising:
an observables component that computes a thermodynamic observable of the molecule based on the partition function.

6. The system of claim 5, wherein the thermodynamic observable is at least one member selected from the group consisting of entropy, internal energy, heat capacity, enthalpy, Gibbs free energy, constant volume heat capacity, constant pressure heat capacity, Helmholtz free energy, reaction rate, and a reaction equilibrium constant.

7. A system, comprising:
a memory that stores computer executable components; and
a processor, operably coupled to the memory, and that executes the computer executable components stored in the memory, wherein the computer executable components comprise:
a variational quantum eigensolver (VQE) component that executes a variational quantum eigensolver algorithm on a quantum device to compute a Born-Oppenheimer potential energy surface of a molecule; and
an optimizer component that executes an optimization algorithm used in the variational quantum eigensolver algorithm;
a computations component that computes a partition function based on the Born-Oppenheimer potential energy surface of the molecule, wherein the computations component utilizes a parameterized molecular potential energy function, thus mitigating inherent to the quantum device that executed the variational quantum eigensolver algorithm, wherein the parameterized molecular potential energy function comprises a potential energy loss function employed for a parameterized potential energy surface, and wherein the employment comprises using a plurality of VQE calculations across a range of bond lengths of the molecule, thereby fitting a set of parameters of the VQE calculations.

8. The system of claim 7, wherein the parameterized molecular potential energy function accounts for uneven spacing in vibrational energy levels in the molecule.

9. The system of claim 7, wherein the optimization algorithm further implements an adaptive termination process.

10. The system of claim 7, further comprising:
a vibrational mode component that computes an intramolecular vibrational mode based on the parameterized the molecular potential energy function; and
a partition component that computes the partition function based on the intramolecular vibrational mode.

11. The system of claim 7, further comprising:
an observables component that computes a thermodynamic observable based on the partition function.

12. A computer-implemented method, comprising:
executing, by a system operably coupled to a processor, a variational quantum eigensolver (VQE) algorithm on a quantum computer to compute a potential energy surface of a molecule;
fitting, by the system, a potential energy function to the potential energy surface of the molecule, wherein the fitting comprises employing a potential energy loss function for a parameterized potential energy surface and using a plurality of VQE calculations across a range of bond lengths of the molecule, thereby fitting a set of parameters of the VQE calculations;

computing, by the system, an intramolecular vibrational mode of the molecule based on the potential energy surface fitted with the potential energy function; and computing, by the system, a partition function based on the intramolecular vibrational mode.

13. The computer-implemented method of claim 12, wherein the variational quantum eigensolver algorithm computes the potential energy surface based on a Born-Oppenheimer approximation.

14. The computer-implemented method of claim 12, wherein the optimization algorithm further implements an adaptive termination process.

15. The computer-implemented method of claim 12, further comprising:
computing, by the system, a thermodynamic observable of the molecule based on the partition function.

16. The computer-implemented method of claim 15, wherein the thermodynamic observable is at least one member selected from the group consisting of entropy, internal energy, enthalpy, Gibbs free energy, constant volume heat capacity, constant pressure heat capacity, Helmholtz free energy, reaction rate, and a reaction equilibrium constant.

17. A computer-implemented method, comprising:
executing, by a system operably coupled to a processor, a variational quantum eigensolver (VQE) algorithm on a quantum device to compute a Born-Oppenheimer potential energy surface of a molecule;
computing, by the system, a partition function based on the Born-Oppenheimer potential energy surface; and
utilizing, by the system, a parameterized molecular potential energy function to mitigate noise inherent to the quantum device that executed the variational quantum eigensolver algorithm, wherein the parameterized molecular potential energy function comprises a potential energy loss function employed for a parameterized potential energy surface, and wherein the utilization comprises using a plurality of VQE calculations across a range of bond lengths of the molecule, thereby fitting a set of parameters of the VQE calculations.

18. The computer-implemented method of claim 17, wherein the optimization algorithm further implements an adaptive termination process.

19. The computer-implemented method of claim 17, further comprising:
computing, by the system, an intramolecular vibrational mode based on the parameterized molecular potential energy function; and computing, by the system, the partition function based on the intramolecular vibrational mode.

20. The computer-implemented method of claim 17, further comprising:
computing, by the system, a thermodynamic observable based on the partition function.

21. A computer program product for utilizing quantum computing to determine a thermodynamic observable, the computer program product comprising a non-transitory computer readable medium having program instructions embodied therewith, the program instructions executable by a processor to cause the processor to:
execute, by the processor, a variational quantum eigensolver (VQE) algorithm on a quantum computer to compute a potential energy surface of a molecule;
fit, by the processor, a potential energy function to the potential energy surface of the molecule, wherein the fitting comprises employing a potential energy loss function for a parameterized potential energy surface and using a plurality of VQE calculations across a range of bond lengths of the molecule, thereby fitting a set of parameters of the VQE calculations;
compute, by the processor, an intramolecular vibrational mode of the molecule based on the potential energy surface fitted with the potential energy function; and
compute, by the processor, a partition function based on the intramolecular vibrational mode.

22. The computer program product of claim 21, wherein the optimization algorithm further implements an adaptive termination.

23. The computer program product of claim 21, wherein the potential energy function comprises a Morse potential function.

24. The computer program product of claim 21, wherein the program instructions can further cause the processor to:
compute, by the processor, a thermodynamic observable of the molecule based on the partition function.

25. The computer program product of claim 24, wherein the thermodynamic observable is at least one member selected from the group consisting of entropy, internal energy, enthalpy, Gibbs free energy, heat capacity, constant volume heat capacity, constant pressure heat capacity, Helmholtz free energy, reaction rate, and a reaction equilibrium constant.

* * * * *